US005705612A

United States Patent [19]
Alizon et al.

[11] Patent Number: 5,705,612
[45] Date of Patent: Jan. 6, 1998

[54] NEF PEPTIDE ENCODED BY HUMAN IMMUNODEFIENCY VIRUS TYPE 1 (HIV-1)

[75] Inventors: Marc Alizon; Pierre Sonigo, both of Paris; Cole Stewart, Chatillon; Oliver Danos, Paris; Simon Wain-Hobson, Montigny les Bretonneux, all of France

[73] Assignee: Institut Pasteur and Centre National de la Recherche Scientifique, Paris, France

[21] Appl. No.: 195,024

[22] Filed: Feb. 14, 1994

Related U.S. Application Data

[62] Division of Ser. No. 953,060, Nov. 5, 1992, which is a division of Ser. No. 158,652, Feb. 22, 1988, which is a division of Ser. No. 771,248, Aug. 30, 1985, abandoned.

[30] Foreign Application Priority Data

Oct. 18, 1984 [FR] France .................. 84 16013
Nov. 16, 1984 [GB] United Kingdom ........ 84 29099

[51] Int. Cl.$^6$ .............. C07K 1/00; C07K 14/00; C07K 17/00; A61K 39/21
[52] U.S. Cl. ........... 530/550; 424/188.1; 424/208.1
[58] Field of Search ............ 424/185.1, 187.1, 424/207.1, 208.1, 188.1; 530/350, 826; 514/2; 536/23.72; 435/70.1, 71.1, 172.3

[56] References Cited

U.S. PATENT DOCUMENTS

| | | |
|---|---|---|
| 4,520,113 | 5/1985 | Gallo et al. |
| 4,629,783 | 12/1986 | Cosand |
| 4,708,818 | 11/1987 | Montagnier et al. |
| 4,725,669 | 2/1988 | Essex et al. |
| 4,808,536 | 2/1989 | Chang et al. |
| 5,156,949 | 10/1992 | Luciw et al. |

FOREIGN PATENT DOCUMENTS

| | | |
|---|---|---|
| 0 113 078 | 7/1984 | European Pat. Off. |
| 0 115 459 | 8/1984 | European Pat. Off. |
| 0 199 301 | 10/1986 | European Pat. Off. |
| 0 245 459 B1 | 11/1987 | European Pat. Off. |
| 0 258 404 B1 | 3/1988 | European Pat. Off. |
| WO 84/04327 | 11/1984 | WIPO |
| WO 87/05399 | 9/1987 | WIPO |
| WO 91/04051 | 4/1991 | WIPO |

OTHER PUBLICATIONS

Scheupbach et al., "Serological Analysis of a Subgroup of Human T-Lymphotropic Retroviruses (HTLV-III) Associated with AIDS," *Science*, 224, 503-505 (1984).
Kalyanaraman et al., "Antibodies to the Core Protein of Lymphadenopathy-Associated Virus (LAV) in Patients with AIDS," *Science*, 225, 321-323 (1984).
Robey et al., "Characterization of Envelope and Core Structural Gene Products of HTLV-III with Sera from AIDS Patients," *Science*, 228, 593-595 (1985).
Allan et al., "Major Glycoprotein Antigens That Induce Antibodies in AIDS Patients Are Encoded by HTLV-III," *Science*, 228, 1091-1094 (1985).
Crowl et al., "HTLV-III Env Gene Products Synthesized in *E. coli* are Recognized By Antibodies Present in the Sera of AIDS Patients," *Chemical Abstracts*, 103, p. 190, No. 154983e (1985).
Montagnier et al., "Identification and Antigenicity of the Major Envelope Glycoprotein of Lymphadenopathy-Associated Virus," *Chemical Abstracts*, 103, p. 263, No. 34641v (1985).
Weiss et al., "Neutralization of Human T-Lymphotropic Virus Type III by Sera of AIDS and AIDS-Risk Patients," *Nature*, 316, 69-72 (1985).
Barin et al., "Virus Envelope Protein of HTLV-III Represents Major Target Antigen for Antibodies in AIDS Patients," *Science*, 228, 1094-1096 (1985).
Wain-Hobson et al., "Nucleotide Sequence of the AIDS Virus, LAV," *Cell*, 40, 9-17 (1985).
Muesing et al., "Nucleic Acid Structure and Expression of the Human AIDS/Lymphadenopathy Retrovirus," *Nature*, 313, 450-458 (1985).
Schneider et al., "A Glycopolypeptide (gp 100) is the Main Antigen Detected by HTLV-III Antiserums,"*Chemical Abstracts*, 103, p. 430, No. 52370k (1985).
Sarngadharan et al., "Immunological Properties of HTLV-III Antigens Recognized By Sera of Paatients with AIDS-Related Complex and of Asymptomatic Carriers of HTLV-III Infection," *Chemical Abstracts*, 103, p. 551, No. 121329t (1985).
Alizon et al., "Molecular Cloning of Lymphadenopathy-Associated Virus," *Nature*, 312, 757-760 (1984).
Chang et al., "An HTLV-III Peptide Produced by Recombinant DNA is Immunoreactive With Sera From Patients With AIDS," *Nature*, 315, 151-154 (1985).
Chang et al., "Detection of Antibodies to Human T-Cell Lymphotropic Virus-III (HTLV-III) with an Immunoassay Employing a Recombinant *Escherichia coli*-Derived Viral Antigenic Peptide," *Biotechnology*, 3, 905-909 (1985).

*Primary Examiner*—Christine M. Nucker
*Assistant Examiner*—Jeffrey S. Parkin
*Attorney, Agent, or Firm*—Finnegan, Henderson, Farabow, Garrett & Dunner, L.L.P.

[57] ABSTRACT

The complete nucleotide sequence of a proviral molecular clone of the lymphadenopathy-associated virus, LAV, was ascertained. Recombinant phage clones were isolated from a genomic library of LAV-infected human T-lymphocyte DNA. The insert of recombinant phase λJ19 was sequenced according to the dideoxy chain termination method. In addition to the retroviral structural genes gag, pol, and env, a novel open reading frame (ORF) was identified in the 3' region of the viral genome and designated ORF-R. The ORF-R coding region, which has subsequently been renamed nef, encodes a 206 amino acid protein that slightly overlaps the 3' end of the env gene and the 5' portion of the U3 region of the viral long terminal repeat (LTR). Nucleic acids encoding this protein and the precise amino acid sequence of the Nef are disclosed in this application. These products are useful for the generation of immunological reagents to facilitate the detection of LAV.

2 Claims, 25 Drawing Sheets

OTHER PUBLICATIONS

Ratner et al., "Complete Nucleotide Sequence of the AIDS Virus, HTLV–III," *Nature*, 313, 277–284 (1985).

Dreesman et al., "Antibody to Hepatitus B Surface Antigen After a Single Inoculation of Uncoupled Synthetic HBsAg Peptides," *Nature*, 295, 158–160 (1982).

Kitchen et al., "Aetiology of AIDS–Antibodies to Human T–Cell Leukaemia Virus (Type III) in Haemophiliacs," *Nature*, 312, 367–369 (1984).

Essex et al., "Antibodies to Cell Membrane Antigens Associated with Human T–Cell Leukemia Virus in Patients with AIDS," *Science*, 220, 859–862 (1983).

Seiki et al., "Human Adult T–Cell Leukemia Virus: Complete Nucleotide Sequence of the Provirus Genome Integrated in Leukemia Cell DNA," *Proc. Natl. Acad. Sci.*, USA, 80, 3618–3622 (1983).

"Centocor Unveils R–DNA AIDS Assay; Faces FDA," *Biotechnol. Newswatch*, vol. 5, p. 3, Abstract No. 03–10–003226 (1985).

Arya et al., "Homology of Genome of AIDS–Associated Virus With Genomes of Human T–Cell Leukemia Viruses," *Science*, 225, 927–930 (1984).

Kamlehar, S. et al. Science 262:1680–1685 (1993).

Guy, B. et al. Nature 330:266–269 (1987).

```
              N  R  G  E  Q  E  M  E  P  V  D  P  R  L  E  P  W  K  H  P  G  S  Q  P  K
               T  F  E  S  K  K  W  S  Q  *  I  L  D  *  S  P  G  S  I  Q  E  V  S  L
CAACAGAGGAGAGCAAGAAATGGAGCCAGTAGATCCTAGACTAGAGCCCTGGAAGCATCCAGGAAGTCAGCCTAA
    5290      5300      5310      5320      5330      5340      5350

P  S  L  F  H  N  K  S  L  R  H  L  L  W  Q  E  E  A  E  T  A  T  K  T  S
       Q  V  C  F  T  T  K  A  L  G  I  S  Y  G  R  K  K  R  R  Q  R  R  R  P  P
        K  F  V  S  Q  Q  K  P  *  A  S  P  M  A  G  R  S  G  D  S  D  E  D  L  L
CCAAGTTTGTTTCACAACAAAAGCCTTAGGCATCTCCTATGGCAGGAAGAAGCGGAGACAGCGACGAAGACCTCCT
    5410      5420      5430      5440      5450      5460      5470

S  T  C  N  A  T  Y  T  N  S  N  S  S  I  S  S  S  N  N  N  S  N  S  C  V
       V  H  V  M  Q  P  I  Q  I  A  I  A  A  L  V  V  A  I  I  I  A  I  V  V
        Y  M  *  C  N  L  Y  K  *  Q  *  Q  H  *  *  *  Q  *  *  *  Q  *  L  C  C
AGTACATGTAATGCAACCTATACAAATAGCAATAGCAGCATTAGTAGTAGCAATAATAATAGCAATAGTTGTGTGG
    5530      5540      5550      5560      5570      5580      5590

N  R  Q  V  N  *  *  T  N  R  K  S  R  R  Q  W  Q  *  E  *  R  R  N  I  S
       I  D  R  L  I  D  R  L  I  E  R  A  E  D  S  G  N  E  S  E  G  E  I  S  A
        *  T  G  *  L  I  D  *  *  K  E  Q  K  T  V  A  M  R  V  K  E  K  Y  Q
AATAGACAGGTTAATTGATAGACTAATAGAAAGAGCAGAAGACAGTGGCAATGAGAGTGAAGGAGAAATATCAGCA
    5650      5660      5670      5680      5690      5700      5710

Y  *  *  S  V  V  L  Q  K  N  C  G  S  Q  S  I  M  G  Y  L  C  G  R  K  Q
       I  D  D  L  *  C  Y  R  K  I  V  G  H  S  L  L  W  G  T  C  V  E  G  S  N
        L  M  I  C  S  A  T  E  K  L  W  V  T  V  Y  Y  G  V  P  V  W  K  E  A  T
TATTGATGATCTGTAGTGCTACAGAAAAATTGTGGGTCACAGTCTATTATGGGGTACCTGTGTGGAAGGAAGCCAAC
    5770      5780      5790      5800      5810      5820      5830

R  Y  I  M  F  G  P  H  M  P  V  Y  P  Q  T  P  T  H  K  K  *  Y  W  *  *
       G  T  *  C  L  G  H  T  C  L  C  T  H  R  P  Q  P  T  R  S  S  I  G  K  C
        V  H  N  V  W  A  T  H  A  C  V  P  T  D  P  N  P  Q  E  V  V  L  V  [N  V]
AGGTACATAATGTTTGGGCCACACATGCCTGTGTACCCACAGACCCCAACCCACAAGAAGTAGTATTGGTAAATGT
    5890      5900      5910      5920      5930      5940      5950

C  M  R  I  *  S  V  Y  G  I  K  A  *  S  H  V  *  N  *  P  H  S  V  L  V
       A  *  G  Y  N  Q  F  M  G  S  K  P  K  A  M  C  K  I  N  P  T  L  C  *  F
        H  E  D  I  I  S  L  W  D  Q  S  L  K  P  C  V  K  L  T  P  L  C  V  S  U
TGCATGAGGATATAATCAGTTTATGGGATCAAAGCCTAAAGCCATGTCTAAAATTAACCCCACTCTGTGTTAGTTT
    6010      6020      6030      6040      6050      6060      6070

I  P  I  V  V  A  G  K  *  *  W  R  K  E  R  *  K  T  A  L  S  I  S  A  Q
       Y  Q  *  *  *  R  G  N  D  D  G  E  R  R  D  K  K  L  L  F  Q  Y  Q  H  K
        T [N  S  S] S  G  E  M  M  M  E  K  G  E  I  K [N  C  S] F [N  I  S] T  S
ATACCAATAGTAGTAGCGGGGAAATGATGATGGAGAAAGGAGAGATAAAAAACTGCTCTTTCAATATCAGCACAAG
    6130      6140      6150      6160      6170      6180      6190

L  I  *  Y  Q  *  I  M  I  L  P  A  I  R  *  Q  V  V  T  P  Q  S  L  H  R
       *  Y  N  T  N  R  *  *  Y  Y  Q  L  Y  V  D  K  L  *  H  L  S  H  Y  T  G
        D  I  I  P  I  D [N  D  T] T  S  Y  T  L  T  S  C [N  T  S] V  I  T  Q  A
TTGATATAATACCAATAGATAATGATACTACCAGCTATACGTTCACAAGTTGTAACACCTCAGTCATTACACAGGG
    6250      6260      6270      6280      6290      6300      6310

```
P  G  S  Q  P  K  T  A  C  I  T  C  Y  C  K  K  C  C  F  H  C
 Q  E  V  S  L  K  L  L  V  P  L  A  I  V  K  S  V  A  F  I  A
CAGGAAGTCAGCCTAAAACTGCTTGTACCACTTGCTATTGTAAAAGTGTTGCTTTCATTG
     5350      5360      5370      5380      5390      5400

A  T  K  T  S  S  R  Q  S  D  S  S  S  F  S  I  K  A  V  S
 Q  R  R  R  P  P  Q  G  S  Q  T  H  Q  V  S  L  S  K  Q  *  V
  S  D  E  D  L  L  K  A  V  R  L  I  K  F  L  Y  Q  S  S  K  *
AGCGACGAAGACCTCCTCAAGGCAGTCAGACTCATCAAGTTTCTCTATCAAAGCAGTAAGT
     5470      5480      5490      5500      5510      5520

S  N  S  C  V  V  H  S  N  H  R  I  *  E  N  I  K  T  K  K
  I  A  I  V  V  W  S  I  V  I  I  E  Y  R  K  I  L  R  Q  R  K
 *  Q  *  L  C  G  P  *  *  S  *  N  I  G  K  Y  *  D  K  E  K
TAGCAATAGTTGTGTGGTCCATAGTAATCATAGAATATAGGAAAATATTAAGACAAAGAAA
     5590      5600      5610      5620      5630      5640

R  R  N  I  S  T  C  G  D  G  G  G  N  G  A  P  C  S  L  G
   G  E  I  S  A  L  V  E  M  G  V  E  M  G  H  H  A  P  W  D
     K  E  K  Y  Q  H  L  W  R  W  G  W  K  W  G  T  M  L  L  G  I
AAGGAGAAATATCAGCACTTGTGGAGATGGGGGTGGAAATGGGGCACCATGCTCCTTGGGA
     5710      5720      5730      5740      5750      5760

C  G  P  K  Q  P  P  L  Y  F  V  H  Q  M  L  K  H  M  I  Q
  V  E  G  S  N  H  H  S  I  L  C  I  R  C  *  S  I  *  Y  R
   V  W  K  E  A  T  T  T  L  F  C  A  S  D  A  K  A  Y  D  T  E
TGTGGAAGGAAGCAACCACCACTCTATTTTGTGCATCAGATGCTAAAGCATATGATACAG
     5830      5840      5850      5860      5870      5880

*  Y  W  *  M  *  Q  K  I  L  T  C  G  K  M  T  W  *  N  R
  S  I  G  K  C  D  R  K  F  *  H  V  E  K  *  H  G  R  T  D
   V  V  L  V  N  V  T  E  N  F  N  M  W  K  N  D  M  V  E  Q  M
TAGTATTGGTTAAATGTGACAGAAAATTTTAACATGTGGAAAAATGACATGGTAGAACAGA
     5950      5960      5970      5980      5990      6000

H  S  V  L  V  *  S  A  L  I  W  G  M  L  L  I  P  I  V  V
  T  L  C  *  F  K  V  H  *  F  G  E  C  Y  *  Y  Q  *  *  *
   P  L  C  V  S  L  K  C  T  D  L  G  N  A  T  N  T  N  S  S  N
CACTCTGTGTTAGTTTAAAGTGCACTGATTTGGGGAATGCTACTAATACCAATAGTAGTA
     6070      6080      6090      6100      6110      6120

S  I  S  A  Q  A  *  E  V  R  C  R  K  N  M  H  F  F  I  N
   Q  Y  Q  H  K  H  K  R  *  G  A  E  R  I  C  I  F  L  *  T
 F  N  I  S  T  S  I  R  G  K  V  Q  K  E  Y  A  F  F  Y  K  L
TCAATATCAGCACAAGCATAAGAGGTAAGGTGCAGAAAGAATATGCATTTTTTTATAAAC
     6190      6200      6210      6220      6230      6240

Q  S  L  H  R  P  V  Q  R  Y  P  L  S  Q  F  P  Y  I  I  V
  S  H  Y  T  G  L  S  K  G  I  L  *  A  N  S  H  T  L  L  C
   S  V  I  T  Q  A  C  P  K  V  S  F  E  P  I  P  I  H  Y  C  A
CAGTCATTACACAGGCCTGTCCAAAGGTATCCTTTGAGCCAATTCCCATACATTATTGTG
     6310      6320      6330      6340      6350      6360

```
  P  C  W  F  C  D  S  K  M  *  *  *  D  V  Q  W  N  R  T  M  Y  K  C  Q
     P  A  G  F  A  I  L  R  C  N  N  K  T  F  N  G  T  G  P  C  T  N  V  S
CCCCGGCTGGTTTTGCGATTCTAAAATGTAATAATAAGACGTTCAATGGAACAGGACCATGTACAAATGTCAGC
       6370      6380      6390      6400      6410      6420      6430

C  C  *  M  A  V  *  Q  K  K  R  *  *  L  D  L  P  I  S  Q  T  M  L  K  P
  A  V  E  W  Q  S  S  R  R  R  G  S  N  *  I  C  Q  F  H  R  Q  C  *  N  H
  L  L  N  G  S  L  A  E  E  E  V  V  I  R  S  A  N  F  T  D  N  A  K  T
TGCTGTTGAATGGCAGTCTAGCAGAAGAAGAGGTAGTAATTAGATCTGCCAATTTCACAGACAATGCTAAAACCA
       6490      6500      6510      6520      6530      6540      6550

P  T  T  I  Q  E  K  V  S  V  S  R  G  D  Q  G  E  H  L  L  Q  *  E  K  *
  Q  Q  Q  Y  K  K  K  Y  P  Y  P  E  G  T  R  E  S  I  C  Y  N  R  K  N  R
  N  N  N  T  R  K  S  I  R  I  Q  R  G  P  G  R  A  F  V  T  I  G  K  I
CCAACAACAATACAAGAAAAAGTATCCGTATCCAGAGGGGACCAGGGGAGAGCATTTGTTACAATAGGAAAAATAG
       6610      6620      6630      6640      6650      6660      6670

M  P  L  *  N  R  *  L  A  N  *  E  N  N  L  E  I  I  K  Q  *  S  L  S  N
  C  H  F  K  T  D  S  *  Q  I  K  R  T  I  W  K  *  *  N  N  N  L  *  A  I
  A  T  L  K  Q  I  A  S  K  L  R  E  Q  F  G  N  N  K  I  I  I  F  K  Q
ATGCCACTTTAAAACAGATAGCTAGCAAATTAAGAGAACAATTTGGAAATAATAAAACAATAATCTTTAAGCAA
       6730      6740      6750      6760      6770      6780      6790

E  G  N  F  S  T  V  I  Q  H  N  C  L  I  V  L  G  L  I  V  L  G  V  L  K
  R  G  I  F  L  L  *  F  N  T  T  V  *  *  Y  L  V  *  *  Y  L  E  Y  *  R
  G  E  F  F  Y  C  N  S  T  Q  L  F  N  S  T  W  F  N  S  T  W  S  T  E
GAGGGGAATTTTTCTACTGTAATTCAACACAACTGTTTAATAGTACTTGGTTTAATAGTACTTGGAGTACTGAAG
       6850      6860      6870      6880      6890      6900      6910

E  *  N  N  L  *  T  C  G  R  K  *  E  K  Q  C  M  P  L  P  S  A  D  K  L
  N  K  T  I  Y  K  H  V  A  G  S  R  K  S  N  V  C  P  S  H  Q  R  T  N  *
  I  K  Q  F  I  N  M  W  Q  E  V  G  K  A  M  Y  A  P  P  I  S  G  Q  I
GAATAAAACAATTTATAAACATGTGGCAGGAAGTAGGAAAAGCAATGTATGCCCCTCCCATCAGCGGACAAATTA
       6970      6980      6990      7000      7010      7020      7030

V  I  T  T  M  G  P  R  S  S  D  L  E  E  E  I  *  G  T  I  G  E  V  N  Y
  *  *  Q  Q  W  V  R  D  L  Q  T  W  R  R  R  Y  E  G  Q  L  E  K  *  I  I
  N  N  N  N  G  S  E  I  F  R  P  G  G  G  D  M  R  D  N  W  R  S  E  L
GTAATAACAACAATGGGTCCGAGATCTTCAGACCTGGAGGAGGAGATATGAGGGACAATTGGAGAAGTGAATTAT
       7090      7100      7110      7120      7130      7140      7150

P  R  Q  R  E  E  W  C  R  E  K  K  E  Q  W  E  *  E  L  C  S  L  G  S  W
  Q  G  K  E  K  S  G  A  E  R  K  K  S  S  G  N  R  S  F  V  P  W  V  L  G
  K  A  K  R  R  V  V  Q  R  E  K  R  A  V  G  I  G  A  L  F  L  G  F  L
CCAAGGCAAAGAGAAGAGTGGTGCAGAGAGAAAAAGAGCAGTGGGAATAGGAGCTTTGTTCCTTGGGTTCTTGG
       7210      7220      7230      7240      7250      7260      7270

Y  R  P  D  N  Y  C  L  V  *  C  S  S  R  T  I  C  *  G  L  L  R  R  N  S
  T  G  Q  T  I  I  V  W  Y  S  A  A  A  E  Q  F  A  E  G  Y  *  G  A  T  A
  Q  A  R  Q  L  L  S  G  I  V  Q  Q  Q  N  N  L  L  R  A  I  E  A  Q  Q
TACAGGCCAGACAATTATTGTCTGGTATAGTGCAGCAGCAGAACAATTTGCTGAGGGCTATTGAGGCGCAACAGC
       7330      7340      7350      7360      7370      7380      7390

```
  N  R  T  M  Y  K  C  Q  H  S  T  M  Y  T  W  N  *  N  S  S  I  N  S  T
     T  G  P  C  T  N  V  S  T  V  Q  C  T  H  G  I  R  P  V  V  S  T  Q  L
AACAGGACCATGTACAAATGTCAGCACAGTACAATGTACACATGGAATTAGGCCAGTAGTATCAACTCAAC
     6420      6430      6440      6450      6460      6470      6480

P  I  S  Q  T  M  L  K  P  *  *  Y  S  *  T  N  L  *  K  L  I  V  Q  D
  Q  F  H  R  Q  C  *  N  H  N  S  T  A  E  P  I  C  R  N  *  L  Y  K  T
     N  F  T  D  N  A  K  T  I  I  V  Q  L  N  Q  S  V  E  I  N  C  T  R  P
CAATTTCACAGACAATGCTAAAACCATAATAGTACAGCTGAACCAATCTGTAGAGAATTAATTGTACAAGAC
     6540      6550      6560      6570      6580      6590      6600

F  H  L  L  Q  *  E  K  *  E  I  *  D  K  H  I  V  T  L  V  E  Q  N  G
  S  I  C  Y  N  R  K  N  R  K  Y  E  T  S  T  K  *  H  *  *  S  K  M  E
     A  F  V  T  I  G  K  I  G  N  M  R  Q  A  H  C  N  I  S  R  A  K  W  N
AGCATTTGTTACAATAGGAAAAATAGGAAATATGAGACAAGCACATTGTAACATTAGTAGAGCAAAATGGA
     6660      6670      6680      6690      6700      6710      6720

I  I  K  Q  *  S  L  S  N  P  Q  E  G  T  Q  K  L  *  R  T  V  L  I  V
  *  *  N  N  N  L  *  A  I  L  R  R  G  P  R  N  C  N  A  Q  F  *  L  W
     N  K  I  I  I  F  K  Q  S  S  G  G  D  P  E  I  V  T  H  S  F  N  C  G
TAATAAAACAATAATCTTTAAGCAATCCTCAGGAGGGGACCCAGAAAATTGTAACGCACAGTTTTAATTGTG
     6780      6790      6800      6810      6820      6830      6840

C  L  I  V  L  G  V  L  K  G  Q  I  T  L  K  E  V  T  Q  S  H  S  H  A
  V  *  *  Y  L  E  Y  *  R  V  K  *  H  *  R  K  *  H  N  H  T  P  M  Q
     P  N  S  T  W  S  T  E  G  S  N  N  T  E  G  S  D  T  I  T  L  P  C  R
TTTTAATAGTACTTGGAGTACTGAAGGGTCAAATAACACTGAAGGAAGTGACACAATCACACTCCCATGCA
     6900      6910      6920      6930      6940      6950      6960

M  P  L  P  S  A  D  K  L  D  V  H  Q  I  L  Q  G  C  Y  *  Q  E  M  V
  C  P  S  H  Q  R  T  N  *  M  F  I  K  Y  Y  R  A  A  I  N  K  R  W  W
     A  P  P  I  S  G  Q  I  R  C  S  S  N  I  T  G  L  L  L  T  R  D  G  G
TGCCCCTCCCATCAGCGGACAAATTAGATGTTCATCAAATATTACAGGGCTGCTATTAACAAGAGATGGTG
     7020      7030      7040      7050      7060      7070      7080

*  G  T  I  G  E  V  N  Y  I  N  I  K  *  *  K  L  N  H  *  E  *  H  P
  E  G  Q  L  E  K  *  I  I  *  I  *  S  S  K  N  *  T  I  R  S  S  T  H
     R  D  N  W  R  S  E  L  Y  K  Y  K  V  V  K  I  E  P  L  G  V  A  P  T
GAGGGACAATTGGAGAAGTGAATTATATAAATATAAAGTAGTAAAAATTGAACCATTAGGAGTAGCACCCA
     7140      7150      7160      7170      7180      7190      7200

*  E  L  C  S  L  G  S  W  E  Q  Q  E  A  L  W  A  H  G  Q  *  R  *  R
  R  S  F  V  P  W  V  L  G  S  S  R  K  H  Y  G  R  T  V  N  D  A  D  G
     G  A  L  F  L  G  F  L  G  A  A  G  S  T  M  G  A  R  S  M  T  L  T  V
AGGAGCTTTGTTCCTTGGGTTCTTGGGAGCAGCAGGAAGCACTATGGGCGCACGGTCAATGACGCTGACGG
     7260      7270      7280      7290      7300      7310      7320

C  *  G  L  L  R  R  N  S  I  C  C  N  S  Q  S  G  A  S  S  S  S  R  Q
  A  E  G  Y  *  G  A  T  A  S  V  A  T  H  S  L  G  H  Q  A  A  P  G  K
     L  R  A  I  E  A  Q  Q  H  L  L  Q  L  T  V  W  G  I  K  Q  L  Q  A  R
GCTGAGGGCTATTGAGGCGCAACAGCATCTGTTGCAACTCACAGTCTGGGGCATCAAGCAGCTCCAGGCAA
     7380      7390      7400      7410      7420      7430      7440

```
N  P  G  C  G  K  I  P  K  G  S  T  A  P  G  D  L  G  L  L  W  K  T  H
 I  L  A  V  E  R  Y  L  K  D  Q  Q  L  L  G  I  W  G  C  S  G  K  L  I
GAATCCTGGCTGTGGAAAGATACCTAAAGGATCAACAGCTCCTGGGGATTTGGGGTTGCTCTGGAAAACTCATI
      7450      7460      7470      7480      7490      7500      7510

W  N  R  F  G  I  T  *  P  G  W  S  G  T  E  K  L  T  I  T  Q  A  *  Y  I
   G  T  D  L  E  *  H  D  L  D  G  V  G  Q  R  N  *  Q  L  H  K  L  N  T
    E  Q  I  W  N  N  M  T  W  M  E  W  D  R  E  I  N  N  Y  T  S  L  I  H
TGGACAGATTTGGAATAACATGACCTGGATGGAGTGGGACAGAGAAATTAACAATTACACAAGCTTAATACAT
      7570      7580      7590      7600      7610      7620      7630

N  Y  W  N  *  I  N  G  Q  V  C  S  I  G  L  T  *  Q  I  G  C  G  I  *  K
   I  I  G  I  R  *  M  G  K  F  V  E  L  V  *  H  N  K  L  A  V  V  Y  K
    L  L  E  L  D  K  W  A  S  L  W  N  W  F  N  I  T  N  W  L  W  Y  I  K
AATTATTGGAATTAGATAAATGGGCAAGTTTGTGGAATTGGTTTAACATAACAAATTGGCTGTGGTATATAAAA
      7690      7700      7710      7720      7730      7740      7750

L  L  Y  F  L  *  *  I  E  L  G  R  D  I  H  H  Y  R  F  R  P  T  S  Q  P
   C  C  T  F  Y  S  E  *  S  *  A  G  I  F  T  I  I  V  S  D  P  P  P  N
    A  V  L  S  I  V  N  R  V  R  Q  G  Y  S  P  L  S  F  Q  T  H  L  P  T
TTGCTGTACTTTCTATAGTGAATAGAGTTAGGCAGGGATATTCACCATTATCGTTTCAGACCCACCTCCCAACC
      7810      7820      7830      7840      7850      7860      7870

R  E  T  E  T  D  P  F  D  *  *  T  D  P  *  H  L  S  G  T  I  C  G  A  L
   E  R  Q  R  Q  I  H  S  I  S  E  R  I  L  S  T  Y  L  G  R  S  A  E  P
    R  D  R  D  R  S  I  R  L  V  N  G  S  L  A  L  I  W  D  D  L  R  S  L
AGAGAGACAGAGACAGATCCATTCGATTAGTGAACGGATCCTTAGCACTTATCTGGGACGATCTGCGGAGCCTT
      7930      7940      7950      7960      7970      7980      7990

T  R  I  V  E  L  L  G  R  R  G  W  E  A  L  K  Y  W  W  N  L  L  Q  Y  W
   R  G  L  W  N  F  W  D  A  G  G  G  K  P  S  N  I  G  G  I  S  Y  S  I
    E  D  C  G  T  S  G  T  Q  G  V  G  S  P  Q  I  L  V  E  S  P  T  V  L
ACGAGGATTGTGGAACTTCTGGGACGCAGGGGGTGGGAAGCCCTCAAATATTGGTGGAATCTCCTACAGTATTC
      8050      8060      8070      8080      8090      8100      8110

A  I  A  V  A  E  G  T  D  R  V  I  E  V  V  Q  G  A  C  R  A  I  R  H  I
   P  *  Q  *  L  R  G  Q  I  G  L  *  K  *  Y  K  E  L  V  E  L  F  A  T
    H  S  S  S  *  G  D  R  *  G  Y  R  S  S  T  R  S  L  *  S  Y  S  P  H
GCCATAGCAGTAGCTGAGGGGACAGATAGGGTTATAGAAGTAGTACAAGGAGCTTGTAGAGCTATTCGCCACAT
      8170      8180      8190      8200      8210      8220      8230

G  W  Q  V  V  K  K  *  C  G  W  M  A  Y  C  K  G  K  N  E  T  S  *  A  S
   G  G  K  W  S  K  S  S  V  V  G  W  P  T  V  R  E  R  M  R  R  A  E  P
    V  A  S  G  Q  K  V  V  W  L  D  G  L  L  *  G  K  E  *  D  E  L  S  Q
GGGTGGCAAGTGGTCAAAAAGTAGTGTGGTTGGATGGCCTACTGTAAGGGAAAGAATGAGACGAGCTGAGCCAG
      8290      8300      8310      8320      8330      8340      8350

S  N  H  K  *  Q  Y  S  S  Y  Q  C  C  L  C  L  A  R  S  T  R  G  G  G  G
   A  I  T  S  S  N  T  A  A  T  N  A  A  C  A  W  L  F  A  Q  E  E  E  E
    Q  S  Q  V  A  I  Q  Q  L  P  M  L  L  V  P  G  *  K  H  K  R  R  R  R
AGCAATCACAAGTAGCAATACAGCAGCTACCAATGCTGCTTGTGCCTGGCTAGAAGCACAAGAGGAGGAGGAGG
      8410      8420      8430      8440      8450      8460      8470

```
  W  K  T  H  L  H  H  C  C  A  L  E  C  *  L  E  *  *  I  S
     G  K  L  I  C  T  T  A  V  P  W  N  A  S  W  S  N  K  S  L
CTGGAAAACTCATTTGCACCACTGCTGTGCCCTTGGAATGCTAGTTGGAGTAATAAATCTC
      7510      7520      7530      7540      7550      7560

Q  A  *  Y  I  P  *  L  K  N  R  K  T  S  K  K  R  M  N  K
   K  L  N  T  F  L  N  *  R  I  A  K  P  A  R  K  E  *  T  R
    S  L  I  H  S  L  I  E  E  S  Q  N  Q  Q  E  K  N  E  Q  E
CAAGCTTAATACATTCCTTAATTGAAGAATCGCAAAACCAGCAAGAAAAGAATGAACAAG
      7630      7640      7650      7660      7670      7680

C  G  I  *  K  Y  S  *  *  *  *  E  A  W  *  V  *  E  *  F
   V  V  Y  K  N  I  H  N  D  S  R  R  L  G  R  F  K  N  S  F
     W  Y  I  K  I  F  I  M  I  V  G  G  L  V  G  L  R  I  V  F
TGTGGTATATAAAAATATTCATAATGATAGTAGGAGGCTTGGTAGGTTTAAGAATAGTTT
      7750      7760      7770      7780      7790      7800

P  T  S  Q  P  R  G  D  P  T  G  P  K  E  *  K  K  K  V  E
   P  P  P  N  P  E  G  T  R  Q  A  R  R  N  R  R  R  R  W  R
     H  L  P  T  P  R  G  P  D  R  P  E  G  I  E  E  E  G  G  E
CCACCTCCCAACCCCGAGGGGACCCGACAGGCCCGAAGGAATAGAAGAAGAAGGTGGAG
      7870      7880      7890      7900      7910      7920

I  C  G  A  L  C  L  F  S  Y  H  R  L  R  D  L  L  L  I  V
   S  A  E  P  C  A  S  S  A  T  T  A  *  E  T  Y  S  *  L  *
     L  R  S  L  V  P  L  Q  L  P  P  L  E  R  L  T  L  D  C  N
TCTGCGGAGCCTTGTGCCTCTTCAGCTACCACCGCTTGAGAGACTTACTCTTGATTGTA
      7990      8000      8010      8020      8030      8040

L  L  Q  Y  W  S  Q  E  L  K  N  S  A  V  S  L  L  N  A  T
   S  Y  S  I  G  V  R  N  *  R  I  V  L  L  A  C  S  M  P  Q
     P  T  V  L  E  S  G  T  K  E  *  C  C  *  L  A  Q  C  H  S
TCCTACAGTATTGGAGTCAGGAACTAAAGAATAGTGCTGTTAGCTTGCTCAATGCCACA
      8110      8120      8130      8140      8150      8160

A  I  R  H  I  P  R  R  I  R  Q  G  L  E  R  I  L  L  *  D
   L  F  A  T  Y  L  E  E  *  D  R  A  W  K  G  F  C  Y  K  M
     Y  S  P  H  T  *  K  N  K  T  G  L  G  K  D  F  A  I  R  W
CTATTCGCCACATACCTAGAAGAATAAGACAGGGCTTGGAAAGGATTTTGCTATAAGAT
      8230      8240      8250      8260      8270      8280

T  S  *  A  S  S  R  W  G  G  S  S  I  S  R  P  G  K  T  W
   R  A  E  P  A  A  D  G  V  G  A  A  S  R  D  L  E  K  H  G
     E  L  S  Q  Q  Q  M  G  W  E  Q  H  L  E  T  W  K  N  M  E
CGAGCTGAGCCAGCAGCAGATGGGGTGGGAGCAGCATCTCGAGACCTGGAAAAACATGG
      8350      8360      8370      8380      8390      8400

Q  G  G  G  G  G  F  S  S  H  T  S  G  T  F  K  T  N  D  L
   E  E  E  E  V  G  F  P  V  T  P  Q  V  P  L  R  P  M  T  Y
     R  R  R  R  R  W  V  F  Q  S  H  L  R  Y  L  *  D  Q  *  L  T
GAGGAGGAGGAGGGGGTTTTCCAGTCACACCTCAGGTACCTTTAAGACCAATGACTTA
      8470      8480      8490      8500      8510      8520

```
           10         20         30         40         50         60
      AAGCTTGCCT TGAGTGCTTC AAGTAGTGTG TGCCCGTCTG TTGTGTGACT CTGGTAACTA
           70         80         90        100        110        120
      GAGATCCCTC AGACCCTTTT AGTCAGTGTG GAAAATCTCT AGCAGTGGCG CCCGAACAGG
          130        140        150        160        170        180
      GACTTGAAAG CGAAAGGGAA ACCAGAGGAG CTCTCTCGAC GCAGGACTCG GCTTGCTGAA
          190        200        210        220        230        240
      GCGCGCACGG CAAGAGGCGA GGGGAGGCGA CTGGTGAGTA CGCCAAAAAT TTTGACTAGC
          250        260        270        280        290        300
      GGAGGCTAGA AGGAGAGAGA TGGGTGCGAG AGCGTCAGTA TTAAGCGGGG GAGAATTAGA
          310        320        330        340        350        360
      TCGATCGGAA AAAATTCGGT TAAGGCCAGG GGCAAGAAA AAATATAAAT TAAAACATAT
          370        380        390        400        410        420
      AGTATGGGCA AGCAGGGAGC TAGAACGATT CGCTGTTAAT CCTGGCCTGT TAGAAACATC
          430        440        450        460        470        480
      AGAAGGCTGT AGACAAATAC TGGGACAGCT ACAACCATCC CTTCAGACAG GATCAGAAGA
          490        500        510        520        530        540
      ACTTAGATCA TTATATAATA CAGTAGCAAC CCTCTATTGT GTGCATCAAA GGATAGAGAT
          550        560        570        580        590        600
      AAAAGACACC AAGGAAGCTT TAGACAAGAT AGAGGAAGAG CAAAACAAAA GTAAGAAAAA
          610        620        630        640        650        660
      AGCACAGCAA GCAGCAGCTG ACACAGGACA CAGCAGCCAG GTCAGCCAAA ATTACCCTAT
          670        680        690        700        710        720
      AGTGCAGAAC ATCCAGGGGC AAATGGTACA TCAGGCCATA TCACCTAGAA CTTTAAATGC
          730        740        750        760        770        780
      ATGGGTAAAA GTAGTAGAAG AGAAGGCTTT CAGCCCAGAA GTGATACCCA TGTTTTCAGC
          790        800        810        820        830        840
      ATTATCAGAA GGAGCCACCC CACAAGATTT AAACACCATG CTAAACACAG TGGGGGGACA
          850        860        870        880        890        900
      TCAAGCAGCC ATGCAAATGT TAAAAGAGAC CATCAATGAG GAAGCTGCAG AATGGGATAG
          910        920        930        940        950        960
      AGTGCATCCA GTGCATGCAG GGCCTATTGC ACCAGGCCAG ATGAGAGAAC CAAGGGGAAG
          970        980        990       1000       1010       1020
      TGACATAGCA GGAACTACTA GTACCCTTCA GGAACAAATA GGATGGATGA CAAATAATCC
         1030       1040       1050       1060       1070       1080
      ACCTATCCCA GTAGGAGAAA TTTATAAAAG ATGGATAATC CTGGGATTAA ATAAAATAGT
         1090       1100       1110       1120       1130       1140
```

FIG. 19

```
AAGAATGTAT AGCCCTACCA GCATTCTGGA CATAAGACAA GGACCAAAAG AACCCTTTAG
   1150       1160       1170       1180       1190       1200
AGACTATGTA GACCGGTTCT ATAAAACTCT AAGAGCCGAG CAAGCTTCAC AGGAGGTAAA
   1210       1220       1230       1240       1250       1260
AAATTGGATG ACAGAAACCT TGTTGGTCCA AAATGCGAAC CCAGATTGTA AGACTATTTT
   1270       1280       1290       1300       1310       1320
AAAAGCATTG GGACCAGCAG CTACACTAGA AGAAATGATG ACAGCATGTC AGGGAGTGGG
   1330       1340       1350       1360       1370       1380
AGGACCCGGC CATAAGGCAA GAGTTTTGGC TGAAGCAATG AGCCAAGTAA CAAATTCAGC
   1390       1400       1410       1420       1430       1440
TACCATAATG ATGCAAAGAG GCAATTTTAG GAACCAAAGA AAGATTGTTA AGTGTTTCAA
   1450       1460       1470       1480       1490       1500
TTGTGGCAAA GAAGGGCACA TAGCCAGAAA TTGCAGGGCC CCTAGGAAAA AGGGCTGTTG
   1510       1520       1530       1540       1550       1560
GAAATGTGGA AAGGAAGGAC ACCAAATGAA AGATTGTACT GAGAGACAGG CTAATTTTTT
   1570       1580       1590       1600       1610       1620
AGGGAAGATC TGGCCTTCCT ACAAGGGAAG GCCAGGGAAT TTTCTTCAGA GCAGACCAGA
   1630       1640       1650       1660       1670       1680
GCCAACAGCC CCACCAGAAG AGAGCTTCAG GTCTGGGGTA GAGACAACAA CTCCCTCTCA
   1690       1700       1710       1720       1730       1740
GAAGCAGGAG CCGATAGACA AGGAACTGTA TCCTTTAACT TCCCTCAGAT CACTCTTTGG
   1750       1760       1770       1780       1790       1800
CAACGACCCC TCGTCACAAT AAAGATAGGG GGCAACTAA AGGAAGCTCT ATTAGATACA
   1810       1820       1830       1840       1850       1860
GGAGCAGATG ATACAGTATT AGAAGAAATG AGTTTGCCAG GAAGATGGAA ACCAAAAATG
   1870       1880       1890       1900       1910       1920
ATAGGGGGAA TTGGAGGTTT TATCAAAGTA AGACAGTATG ATCAGATACT CATAGAAATC
   1930       1940       1950       1960       1970       1980
TGTGGACATA AAGCTATAGG TACAGTATTA GTAGGACCTA CACCTGTCAA CATAATTGGA
   1990       2000       2010       2020       2030       2040
AGAAATCTGT TGACTCAGAT TGGTTGCACT TTAAATTTTC CCATTAGTCC TATTGAAACT
   2050       2060       2070       2080       2090       2100
GTACCAGTAA AATTAAAGCC AGGAATGGAT GGCCCAAAAG TTAAACAATG GCCATTGACA
   2110       2120       2130       2140       2150       2160
GAAGAAAAAA TAAAAGCATT AGTAGAAATT TGTACAGAAA TGGAAAAGGA AGGGAAAATT
   2170       2180       2190       2200       2210       2220
TCAAAAATTG GGCCTGAAAA TCCATACAAT ACTCCAGTAT TTGCCATAAA GAAAAAAGAC
   2230       2240       2250       2260       2270       2280
AGTACTAAAT GGAGAAAATT AGTAGATTTC AGAGAACTTA ATAAGAGAAC TCAAGACTTC
   2290       2300       2310       2320       2330       2340
TGGGAAGTTC AATTAGGAAT ACCACATCCC GCAGGGTTAA AAAAGAAAAA ATCAGTAACA
   2350       2360       2370       2380       2390       2400
```

*FIG. 20*

```
GTACTGGATG TGGGTGATGC ATATTTTTCA GTTCCCTTAG ATGAAGACTT CAGGAAGTAT
    2410       2420       2430       2440       2450       2460
ACTGCATTTA CCATACCTAG TATAAACAAT GAGACACCAG GGATTAGATA TCAGTACAAT
    2470       2480       2490       2500       2510       2520
GTGCTTCCAC AGGGATGGAA AGGATCACCA GCAATATTCC AAAGTAGCAT GACAAAAATC
    2530       2540       2550       2560       2570       2580
TTAGAGCCTT TTAGAAAACA AAATCCAGAC ATAGTTATCT ATCAATACAT GGATGATTTG
    2590       2600       2610       2620       2630       2640
TATGTAGGAT CTGACTTAGA AATAGGGCAG CATAGAACAA AAATAGAGGA GCTGAGACAA
    2650       2660       2670       2680       2690       2700
CATCTGTTGA GGTGGGGACT TACCACACCA GACAAAAAAC ATCAGAAAGA ACCTCCATTC
    2710       2720       2730       2740       2750       2760
CTTTGGATGG GTTATGAACT CCATCCTGAT AAATGGACAG TACAGCCTAT AGTGCTGCCA
    2770       2780       2790       2800       2810       2820
GAAAAAGACA GCTGGACTGT CAATGACATA CAGAAGTTAG TGGGAAAATT GAATTGGGCA
    2830       2840       2850       2860       2870       2880
AGTCAGATTT ACCCAGGGAT TAAAGTAAGG CAATTATGTA AACTCCTTAG AGGAACCAAA
    2890       2900       2910       2920       2930       2940
GCACTAACAG AAGTAATACC ACTAACAGAA GAAGCAGAGC TAGAACTGGC AGAAAACAGA
    2950       2960       2970       2980       2990       3000
GAGATTCTAA AAGAACCAGT ACATGGAGTG TATTATGACC CATCAAAAGA CTTAATAGCA
    3010       3020       3030       3040       3050       3060
GAAATACAGA AGCAGGGGCA AGGCCAATGG ACATATCAAA TTTATCAAGA GCCATTTAAA
    3070       3080       3090       3100       3110       3120
AATCTGAAAA CAGGAAAATA TGCAAGAACG AGGGGTGCCC ACACTAATGA TGTAAAACAA
    3130       3140       3150       3160       3170       3180
TTAACAGAGG CAGTGCAAAA AATAACCACA GAAAGCATAG TAATATGGGG AAAGACTCCT
    3190       3200       3210       3220       3230       3240
AAATTTAAAC TACCCATACA AAAGGAAACA TGGGAAACAT GGTGGACAGA GTATTGGCAA
    3250       3260       3270       3280       3290       3300
GCCACCTGGA TTCCTGAGTG GGAGTTTGTC AATACCCCTC CTTTAGTGAA ATTATGGTAC
    3310       3320       3330       3340       3350       3360
CAGTTAGAGA AAGAACCCAT AGTAGGAGCA GAAACGTTCT ATGTAGATGG GGCAGCTAGC
    3370       3380       3390       3400       3410       3420
AGGGAGACTA AATTAGGAAA AGCAGGATAT GTTACTAATA GAGGAAGACA AAAAGTTGTC
    3430       3440       3450       3460       3470       3480
ACCCTAACTG ACACAACAAA TCAGAAGACT GAGTTACAAG CAATTCATCT AGCTTTGCAG
    3490       3500       3510       3520       3530       3540
GATTCGGGAT TAGAAGTAAA TATAGTAACA GACTCACAAT ATGCATTAGG AATCATTCAA
    3550       3560       3570       3580       3590       3600
GCACAACCAG ATAAAAGTGA ATCAGAGTTA GTCAATCAAA TAATAGAGCA GTTAATAAAA
    3610       3620       3630       3640       3650       3660
```

*FIG. 21*

```
AAGCAAAAGG TCTATCTGGC ATGGGTACCA GCACACAAAG GAATTGGAGG AAATGAACAA
    3670       3680       3690       3700       3710       3720
GTAGATAAAT TAGTCAGTGC TGGAATCAGG AAAGTACTAT TTTTAGATGG AATAGATAAG
    3730       3740       3750       3760       3770       3780
GCCCAAGATG AACATGAGAA ATATCACAGT AATTGGAGAG CAATGGCTAG TGATTTTAAC
    3790       3800       3810       3820       3830       3840
CTGCCACCTG TAGTAGCAAA AGAAATAGTA GCCAGCTGTG ATAAATGTCA GCTAAAAGGA
    3850       3860       3870       3880       3890       3900
GAAGCCATGC ATGGACAAGT AGACTGTAGT CCAGGAATAT GGCAACTAGA TTGTACACAT
    3910       3920       3930       3940       3950       3950
TTAGAAGGAA AAGTTATCCT GGTAGCAGTT CATGTAGCCA GTGGATATAT AGAAGCAGAA
    3970       3980       3990       4000       4010       4020
GTTATTCCAG CAGAAACAGG GCAGGAAACA GCATACTTTC TTTTAAAATT AGCAGGAAGA
    4030       4040       4050       4060       4070       4080
TGGCCAGTAA AAACAATACA TACAGACAAT GGCAGCAATT TCACCAGTAC TACGGTTAAG
    4090       4100       4110       4120       4130       4140
GCCGCCTGTT GGTGGGCGGG AATCAAGCAG GAATTTGGAA TTCCCTACAA TCCCCAAAGT
    4150       4160       4170       4180       4190       4200
CAAGGAGTAG TAGAATCTAT GAATAAAGAA TTAAAGAAAA TTATAGGCCA GGTAAGAGAT
    4210       4220       4230       4240       4250       4260
CAGGCTGAAC ATCTTAAGAC AGCAGTACAA ATGGCAGTAT TCATCCACAA TTTTAAAAGA
    4270       4280       4290       4300       4310       4320
AAAGGGGGGA TTGGGGGGTA CAGTGCAGGG GAAAGAATAG TAGACATAAT AGCAACAGAC
    4330       4340       4350       4360       4370       4380
ATACAAACTA AAGAATTACA AAAACAAATT ACAAAAATTC AAAATTTTCG GGTTTATTAC
    4390       4400       4410       4420       4430       4440
AGGGACAGCA GAGATCCACT TTGGAAAGGA CCAGCAAAGC TCCTCTGGAA AGGTGAAGGG
    4450       4460       4470       4480       4490       4500
GCAGTAGTAA TACAAGATAA TAGTGACATA AAAGTAGTGC CAAGAAGAAA AGCAAAGATC
    4510       4520       4530       4540       4550       4560
ATTAGGGATT ATGGAAAACA GATGGCAGGT GATGATTGTG TGGCAAGTAG ACAGGATGAG
    4570       4580       4590       4600       4610       4620
GATTAGAACA TGGAAAAGTT TAGTAAAACA CCATATGTAT GTTTCAGGGA AAGCTAGGGG
    4630       4640       4650       4660       4670       4680
ATGGTTTTAT AGACATCACT ATGAAAGCCC TCATCCAAGA ATAAGTTCAG AAGTACACAT
    4690       4700       4710       4720       4730       4740
CCCACTAGGG GATGCTAGAT TGGTAATAAC AACATATTGG GGTCTGCATA CAGGAGAAAG
    4750       4760       4770       4780       4790       4800
AGACTGGCAT CTGGGTCAGG GAGTCTCCAT AGAATGGAGG AAAAGAGAT ATAGCACACA
    4810       4820       4830       4840       4850       4860
AGTAGACCCT GAACTAGCAG ACCAACTAAT TCATCTGTAT TACTTTGACT GTTTTTCAGA
    4870       4880       4890       4900       4910       4920
```

*FIG. 22*

```
CTCTGCTATA AGAAAGGCCT TATTAGGACA TATAGTTAGC CCTAGGTGTG AATATCAAGC
    4930       4940       4950       4960       2970       2980
AGGACATAAC AAGGTAGGAT CTCTACAATA CTTGGCACTA GCAGCATTAA TAACACCAAA
    4990       5000       5010       5020       5030       5040
AAAGATAAAG CCACCTTTGC CTAGTGTTAC GAAACTGACA GAGGATAGAT GGAACAAGCC
    5050       5060       5070       5080       5090       5100
CCAGAAGACC AAGGGCCACA GAGGGAGCCA CACAATGAAT GGACACTAGA GCTTTTAGAG
    5110       5120       5130       5140       5150       5160
GAGCTTAAGA ATGAAGCTGT TAGACATTTT CCTAGGATTT GGCTCCATGG CTTAGGGCAA
    5170       5180       5190       5200       5210       5220
CATATCTATG AAACTTATGG GGATACTTGG GCAGGAGTGG AAGCCATAAT AAGAATTCTG
    5230       5240       5250       5260       5270       5280
CAACAACTGC TGTTTATCCA TTTCAGAATT GGGTGTCGAC ATAGCAGAAT AGGCGTTACT
    5290       5300       5310       5320       5330       5340
CAACAGAGGA GAGCAAGAAA TGGAGCCAGT AGATCCTAGA CTAGAGCCCT GGAAGCATCC
    5350       5360       5370       5380       5390       5400
AGGAAGTCAG CCTAAAACTG CTTGTACCAC TTGCTATTGT AAAAAGTGTT GCTTTCATTG
    5410       5420       5430       5440       5450       5460
CCAAGTTTGT TTCACAACAA AAGCCTTAGG CATCTCCTAT GGCAGGAAGA AGCGGAGACA
    5470       5480       5490       5500       5510       5520
GCGACGAAGA CCTCCTCAAG GCAGTCAGAC TCATCAAGTT TCTCTATCAA AGCAGTAAGT
    5530       5540       5550       5560       5570       5580
AGTACATGTA ATGCAACCTA TACAAATAGC AATAGCAGCA TTAGTAGTAG CAATAATAAT
    5590       5600       5610       5620       5630       5640
AGCAATAGTT GTGTGGTCCA TAGTAATCAT AGAATATAGG AAAATATTAA GACAAAGAAA
    5650       5660       5670       5680       5690       5700
AATAGACAGG TTAATTGATA GACTAATAGA AAGAGCAGAA GACAGTGGCA ATGAGAGTGA
    5710       5720       5730       5740       5750       5760
AGGAGAAATA TCAGCACTTG TGGAGATGGG GGTGGAAATG GGGCACCATG CTCCTTGGGA
    5770       5780       5790       5800       5810       5820
TATTGATGAT CTGTAGTGCT ACAGAAAAAT TGTGGGTCAC AGTCTATTAT GGGGTACCTG
    5830       5840       5850       5860       5870       5880
TGTGGAAGGA AGCAACCACC ACTCTATTTT GTGCATCAGA TGCTAAAGCA TATGATACAG
    5890       5900       5910       5920       5930       5940
AGGTACATAA TGTTTGGGCC ACACATGCCT GTGTACCCAC AGACCCCAAC CCACAAGAAG
    5950       5960       5970       5980       5990       6000
TAGTATTGGT AAATGTGACA GAAAATTTTA ACATGTGGAA AAATGACATG GTAGAACAGA
    6010       6020       6030       6040       6050       6060
TGCATGAGGA TATAATCAGT TTATGGGATC AAAGCCTAAA GCCATGTGTA AAATTAACCC
    6070       6080       6090       6100       6110       6120
CACTCTGTGT TAGTTTAAAG TGCACTGATT TGGGGAATGC TACTAATACC AATAGTAGTA
    6130       6140       6150       6160       6170       6180
```

*FIG. 23*

```
ATACCAATAG TAGTAGCGGG GAAATGATGA TGGAGAAAGG AGAGATAAAA AACTGCTCTT
    6190       6200       6210       6220       6230       6240
TCAATATCAG CACAAGCATA AGAGGTAAGG TGCAGAAAGA ATATGCATTT TTTTATAAAC
    6250       6260       6270       6280       6290       6300
TTGATATAAT ACCAATAGAT AATGATACTA CCAGCTATAC GTTGACAAGT TGTAACACCT
    6310       6320       6330       6340       6350       6360
CAGTCATTAC ACAGGCCTGT CCAAAGGTAT CCTTTGAGCC AATTCCCATA CATTATTGTG
    6370       6380       6390       6400       6410       6420
CCCCGGCTGG TTTTGCGATT CTAAAATGTA ATAATAAGAC GTTCAATGGA ACAGGACCAT
    6430       6440       6450       6460       6470       6480
GTACAAATGT CAGCACAGTA CAATGTACAC ATGGAATTAG GCCAGTAGTA TCAACTCAAC
    6490       6500       6510       6520       6530       6540
TGCTGTTGAA TGGCAGTCTA GCAGAAGAAG AGGTAGTAAT TAGATCTGCC AATTTCACAG
    6550       6560       6570       6580       6590       6600
ACAATGCTAA AACCATAATA GTACAGCTGA ACCAATCTGT AGAAATTAAT TGTACAAGAC
    6610       6620       6630       6640       6650       6660
CCAACAACAA TACAAGAAAA AGTATCCGTA TCCAGAGGGG ACCAGGGAGA GCATTTGTTA
    6670       6680       6690       6700       6710       6720
CAATAGGAAA AATAGGAAAT ATGAGACAAG CACATTGTAA CATTAGTAGA GCAAAATGGA
    6730       6740       6750       6760       6770       6780
ATGCCACTTT AAAACAGATA GCTAGCAAAT TAAGAGAACA ATTTGGAAAT AATAAAACAA
    6790       6800       6810       6820       6830       6840
TAATCTTTAA GCAATCCTCA GGAGGGGACC CAGAAATTGT AACGCACAGT TTTAATTGTG
   .6850       6860       6870       6880       6890       6900
GAGGGGAATT TTTCTACTGT AATTCAACAC AACTGTTTAA TAGTACTTGG TTTAATAGTA
    6910       6920       6930       6940       6950       6960
CTTGGAGTAC TGAAGGGTCA AATAACACTG AAGGAAGTGA CACAATCACA CTCCCATGCA
    6970       6980       6990       7000       7010       7020
GAATAAAACA ATTTATAAAC ATGTGGCAGG AAGTAGGAAA AGCAATGTAT GCCCCTCCCA
    7030       7040       7050       7060       7070       7080
TCAGCGGACA AATTAGATGT TCATCAAATA TTACAGGGCT GCTATTAACA AGAGATGGTG
    7090       7100       7110       7120       7130       7140
GTAATAACAA CAATGGGTCC GAGATCTTCA GACCTGGAGG AGGAGATATG AGGGACAATT
    7150       7160       7170       7180       7190       7200
GGAGAAGTGA ATTATATAAA TATAAAGTAG TAAAAATTGA ACCATTAGGA GTAGCACCCA
    7210       7220       7230       7240       7250       7260
CCAAGGCAAA GAGAAGAGTG GTGCAGAGAG AAAAAAGAGC AGTGGGAATA GGAGCTTTGT
    7270       7280       7290       7300       7310       7320
TCCTTGGGTT CTTGGGAGCA GCAGGAAGCA CTATGGGCGC ACGGTCAATG ACGCTGACGG
    7390       7340       7350       7360       7370       7380
TACAGGCCAG ACAATTATTG TCTGGTATAG TGCAGCAGCA GAACAATTTG CTGAGGGCTA
    7390       7400       7410       7420       7430       7440
```

*FIG. 24*

```
TTGAGGCGCA ACAGCATCTG TTGCAACTCA CAGTCTGGGG CATCAAGCAG CTCCAGGCAA
    7450       7460       7470       7480       7490       7500
GAATCCTGGC TGTGGAAAGA TACCTAAAGG ATCAACAGCT CCTGGGGATT TGGGGTTGCT
    7510       7520       7530       7540       7550       7560
CTGGAAAACT CATTTGCACC ACTGCTGTGC CTTGGAATGC TAGTTGGAGT AATAAATCTC
    7570       7580       7590       7600       7610       7620
TGGAACAGAT TTGGAATAAC ATGACCTGGA TGGAGTGGGA CAGAGAAATT AACAATTACA
    7630       7640       7650       7660       7670       7680
CAAGCTTAAT ACATTCCTTA ATTGAAGAAT CGCAAAACCA GCAAGAAAAG AATGAACAAG
    7690       7700       7710       7720       7730       7740
AATTATTGGA ATTAGATAAA TGGGCAAGTT TGTGGAATTG GTTTAACATA ACAAATTGGC
    7750       7760       7770       7780       7790       7800
TGTGGTATAT AAAAATATTC ATAATGATAG TAGGAGGCTT GCTAGGTTTA AGAATAGTTT
    7810       7800       7810       7820       7830       7840
TTGCTGTACT TTCTATAGTG AATAGAGTTA GGCAGGGATA TTCACCATTA TCGTTTCAGA
    7870       7880       7890       7900       7910       7920
CCCACCTCCC AACCCCGAGG GGACCCGACA GGCCCGAAGG AATAGAAGAA GAAGGTGGAG
    7930       7940       7950       7960       7970       7980
AGAGAGACAG AGACAGATCC ATTCGATTAG TGAACGGATC CTTAGCACTT ATCTGGGACG
    7990       8000       8010       8020       8030       8040
ATCTGCGGAG CCTTGTGCCT CTTCAGCTAC CACCGCTTGA GAGACTTACT CTTGATTGTA
    8050       8060       8070       8080       8090       8100
ACGAGGATTG TGGAACTTCT GGGACGCAGG GGGTGGGAAG CCCTCAAATA TTGGTGGAAT
    8110       8120       8130       8140       8150       8160
CTCCTACAGT ATTGGAGTCA GGAACTAAAG AATAGTGCTG TTAGCTTGCT CAATGCCACA
    8170       8180       8190       8200       8210       8220
GCCATAGCAG TAGCTGAGGG GACAGATAGG GTTATAGAAG TAGTACAAGG AGCTTGTAGA
    8230       8240       8250       8260       8270       8280
GCTATTCGCC ACATACCTAG AAGAATAAGA CAGGGCTTGG AAAGGATTTT GCTATAAGAT
    8290       8300       8310       8320       8330       8340
GGGTGGCAAG TGGTCAAAAA GTAGTGTGGT TGGATGGCCT ACTGTAAGGG AAAGAATGAG
    8350       8360       8370       8380       8390       8400
ACGAGCTGAG CCAGCAGCAG ATGGGGTGGG AGCAGCATCT CGAGACCTGG AAAAACATGG
    8410       8420       8430       8440       8450       8460
AGCAATCACA AGTAGCAATA CAGCAGCTAC CAATGCTGCT TGTGCCTGGC TAGAAGCACA
    8470       8480       8490       8500       8510       8520
AGAGGAGGAG GAGGTGGGTT TTCCAGTCAC ACCTCAGGTA CCTTTAAGAC CAATGACTTA
    8530       8540       8550       8560       8570       8580
CAAGGCAGCT GTAGATCTTA GCCACTTTTT AAAAGAAAAG GGGGGACTGG AAGGGCTAAT
    8590       8600       8610       8620       8630       8640
TCACTCCCAA CGAAGACAAG ATATCCTTGA TCTGTGGATC TACCACACAC AAGGCTACTT
    8650       8660       8670       8680       8690       8700
```

*FIG. 25*

```
CCCTGATTGG CAGAACTACA CACCAGGGCC AGGGGTCAGA TATCCACTGA CCTTTGGATG
    8710       8720       8730       8740       8750       8760
GTGCTACAAG CTAGTACCAG TTGAGCCAGA TAAGGTAGAA GAGGCCAATA AAGGAGAGAA
    8770       8780       8790       8800       8810       8820
CACCAGCTTG TTACACCCTG TGAGCCTGCA TGGAATGGAT GACCCTGAGA GAGAAGTGTT
    8830       8840       8850       8860       8870       8880
AGAGTGGAGG TTTGACAGCC GCCTAGCATT TCATCACGTG GCCCGAGAGC TGCATCCGGA
    8890       8900       8910       8920       8930       8940
GTACTTCAAG AACTGCTGAC ATCGAGCTTG CTACAAGGGA CTTTCCGCTG GGGACTTTCC
    8950       8960       8970       8980       8990       9000
AGGGAGGCGT GGCCTGGGCG GAACTGGGGA GTGGCGAGCC CTCAGATGCT GCATATAAGC
    9010       9020       9030       9040       9050       9060
AGCTGCTTTT TGCCTGTACT GGGTCTCTCT GGTTAGACCA GATTTGAGCC TGGGAGCTCT
    9070       9080       9090       9100       9110       9120
CTGGCTAACT AGGGAACCCA CTGCTTAAGC CTCAATAAAG CTT
```

FIG. 26

NEF PEPTIDE ENCODED BY HUMAN IMMUNODEFIENCY VIRUS TYPE 1 (HIV-1)

This is a division of application Ser. No. 07/953,060, filed Nov. 5, 1992 (pending), which is a division of Ser. No. 07/158,652, filed Feb. 22, 1988 (pending), which is a division of Ser. No. 06/771,248, filed Aug. 30, 1985 (now abandoned).

BACKGROUND OF THE INVENTION

This invention relates to cloned DNA sequences indistinguishable from genomic RNA and DNA of lymphadenopathy-associated virus (LAV), a process for their preparation and their uses. It relates more particularly to stable probes including a DNA sequence which can be used for the detection of the LAV virus or related viruses or DNA proviruses in any medium, particularly biological samples containing any of them. The invention also relates to polypeptides, whether glycosylated or not, encoded by said DNA sequences.

Lymphadenopathy-associated virus (LAV) is a human retrovirus first isolated from the lymph node of a homosexual patient with lymphadenopathy syndrome, frequently a prodrome or a benign form of acquired immune deficiency syndrome (AIDS). Subsequently, other LAV isolates were recovered from patients with AIDS or pre-AIDS. All available data are consistent with the virus being the causative agent of AIDS.

A method for cloning such DNA sequences has already been disclosed in British Patent Application Nr. 84 23659, filed on Sep. 19, 1984. Reference is hereafter made to that application as concerns subject matter in common with the further improvements to the invention disclosed herein.

SUMMARY OF THE INVENTION

The present invention aims at providing additional new means which should not only useful for the detection of LAV or related viruses, (hereafter more generally referred to as "LAV viruses"or "Human Immunodeficiency Virus Type 1" or simply "HIV-1"), but also have more versatility, particularly in detecting specific parts of the genomic RNA of said viruses whose expression products are not always directly detectable by immunological methods.

The present invention further aims at providing polypeptides containing sequences in common with polypeptides encoded by the LAV genomic RNA. It relates even more particularly to polypeptides comprising antigenic determinants included in the proteins encoded and expressed by the LAV genome occurring in nature. An additional object of the invention is to further provide means for the detection of proteins related to LAV virus, particularly for the diagnosis of AIDS or pre-AIDS or, to the contrary, for the detection of antibodies against the LAV virus or proteins related therewith, particularly in patients afflicted with AIDs or pre-AIDS or more generally in asymtomatic carriers and in blood-related products. Finally, the invention also aims at providing immunogenic polypeptides, and more particularly protective polypeptides for use in the preparation of vaccine compositions against AIDS or related syndromes.

The present invention relates to additional DNA fragments, hybridizable with the genomic RNA or LAV as they will be disclosed hereafter, as well as with additional cDNA variants corresponding to the whole genomes of LAV viruses. It further relates to DNA recombinants containing said DNAs or cDNA fragments.

The invention relates more particularly to a cDNA variant corresponding to the whole of LAV retroviral genomes, which is characterized by a series of restriction sites in the order hereafter (from the 5' end to the 3' end).

The coordinates of the successive sites of the whole LAV genome (restriction map) are indicated hereafter too, with respect to the Hind III site (selected as of coordinate 1) which is located in the R region. The coordinates are estimated with an accuracy of ±200 bp:

| | |
|---|---|
| Hind III | 0 |
| Sac I | 50 |
| Hind III | 520 |
| Pst I | 800 |
| Hind III | 1 100 |
| Bgl II | 1 500 |
| Kpn I | 3 500 |
| Kpn I | 3 900 |
| Eco RI | 4 100 |
| Eco RI | 5 300 |
| Sal I | 5 500 |
| Kpn I | 6 100 |
| Bgl II | 6 500 |
| Bgl II | 7 600 |
| Hind III | 7 850 |
| Bam HI | 8 150 |
| Xho I | 8 600 |
| Kpn I | 8 700 |
| Bgl II | 8 750 |
| Bgl II | 9 150 |
| Sac I | 9 200 |
| Hind III | 9 250 |

Another DNA variant according to this invention optionally contains an additional Hind III approximately at the 5 550 coordinate.

Reference is further made to FIG. 1 which shows a more detailed restriction map of said whole DNA (λJ19).

An even more detailed nucleotide sequence of a preferred DNA according to the invention is shown in FIGS. 4–12 hereafter.

The invention further relates to other preferred DNA fragments which will be referred to hereafter.

BRIEF DESCRIPTION OF THE DRAWINGS

Additional features of the invention will appear in the course of the non-limitative disclosure of additional features of preferred DNAs of the invention, as well as of preferred polypeptides according to the invention. Reference will further be had to the drawings in which:

Figure 5:
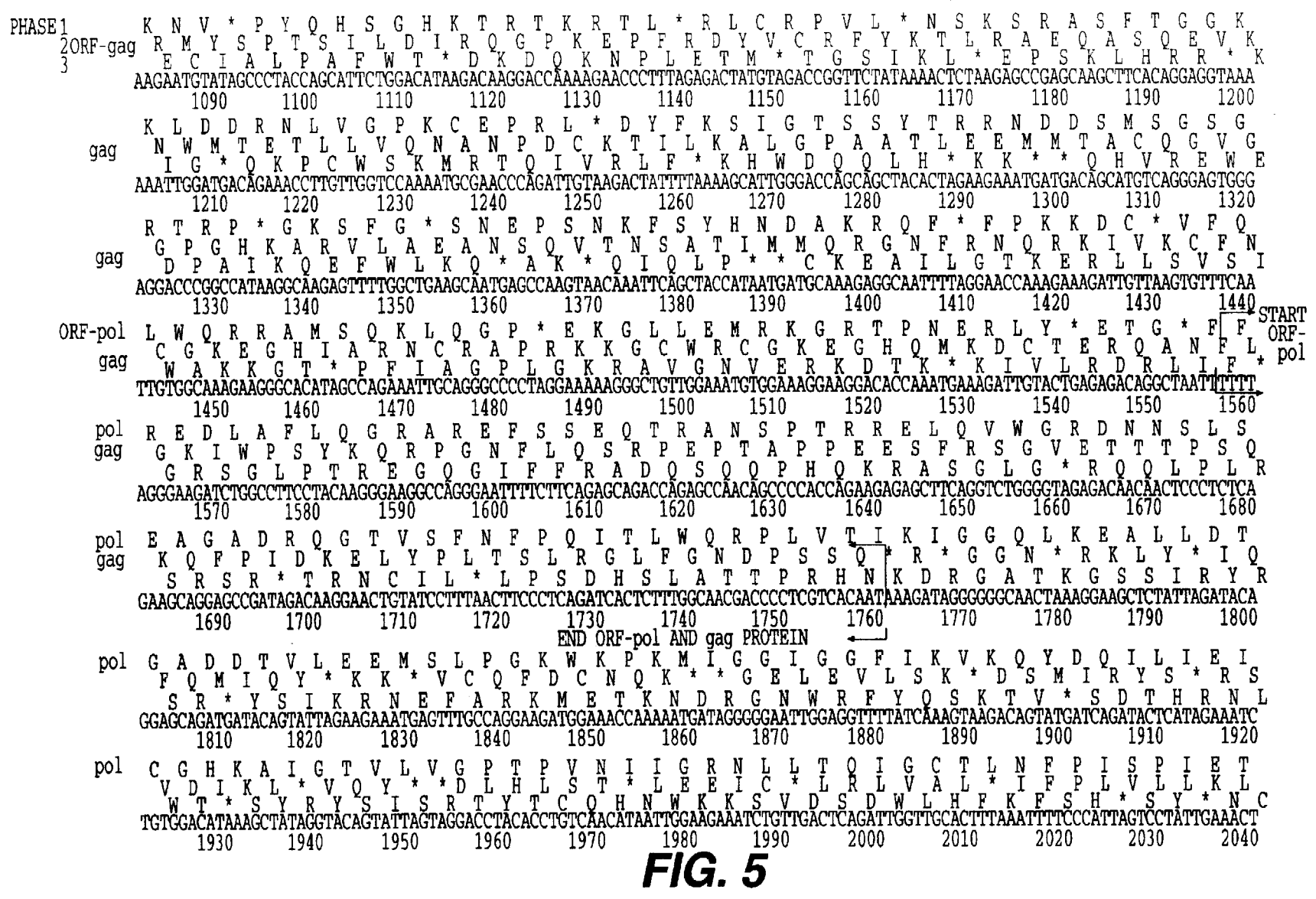
Figure 6:
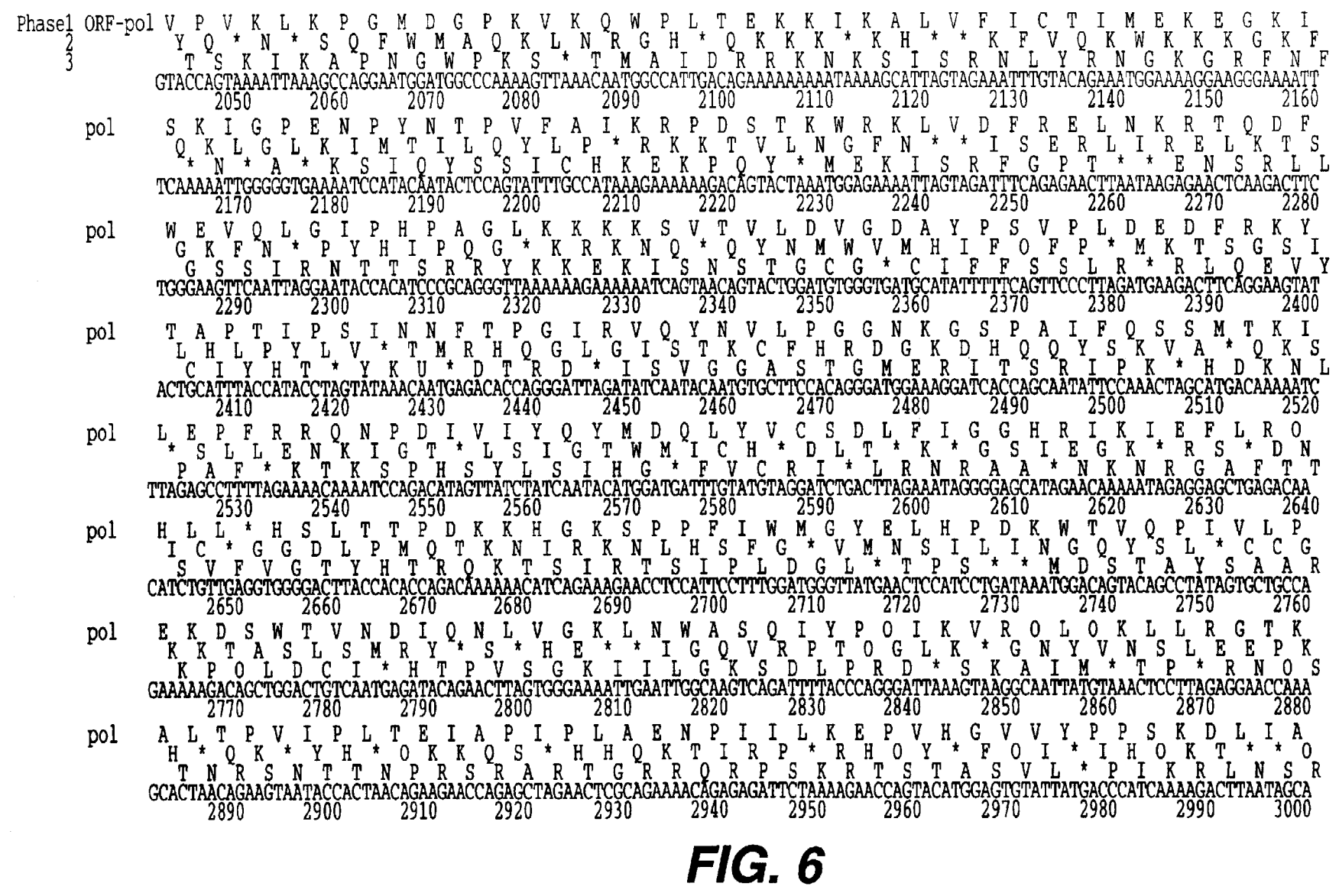
Figure 7:
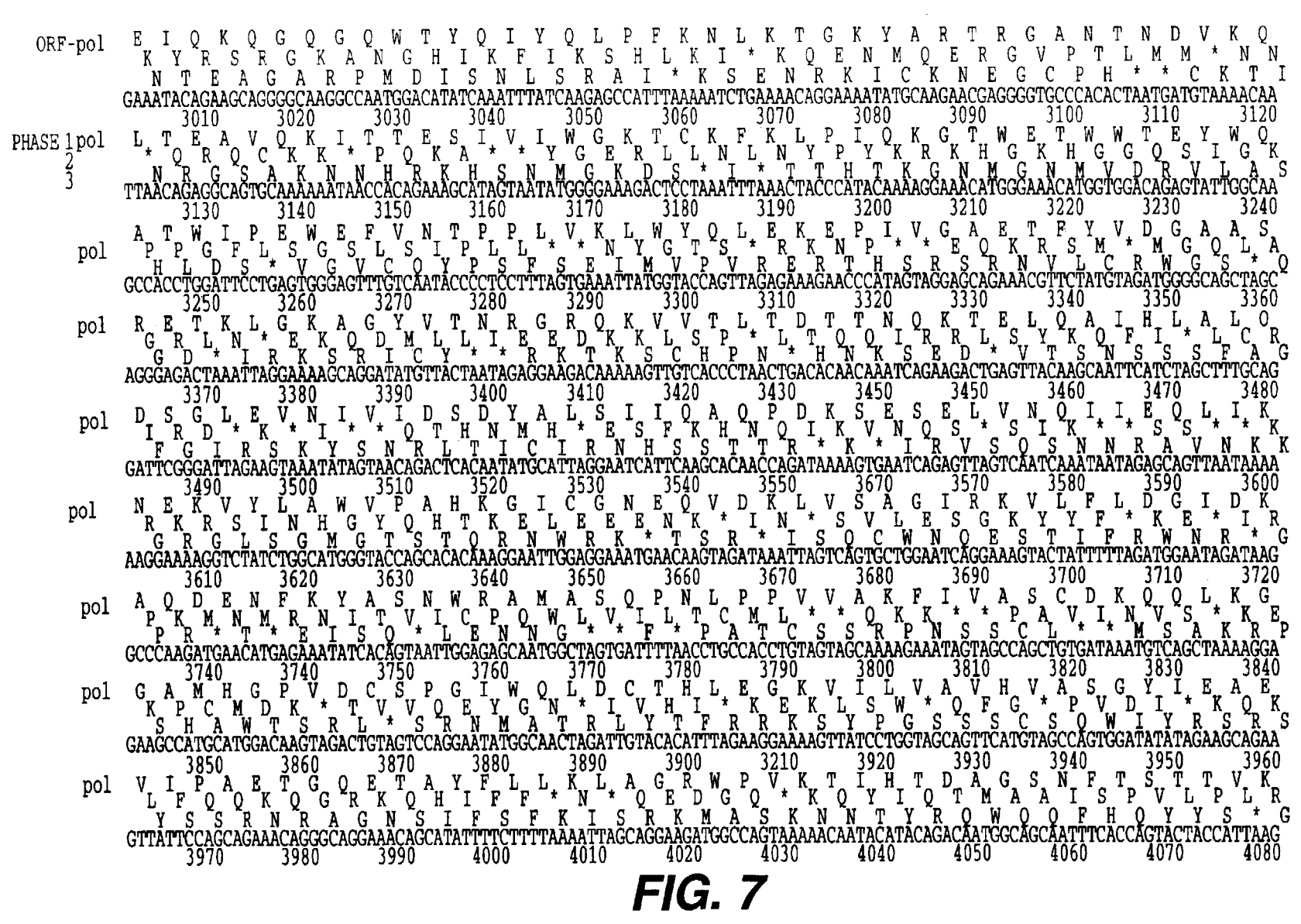
Figure 8:
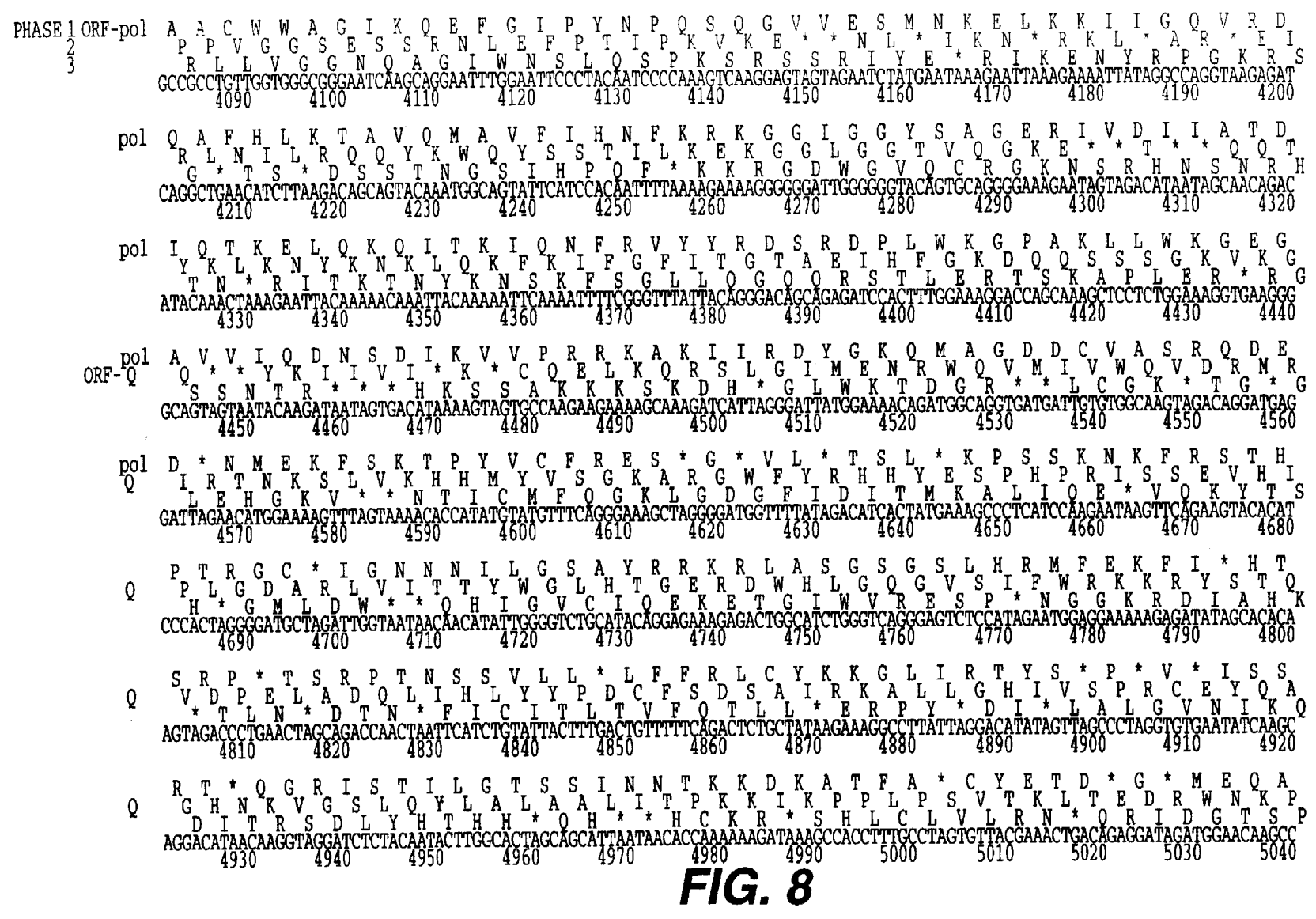
Figure 9:
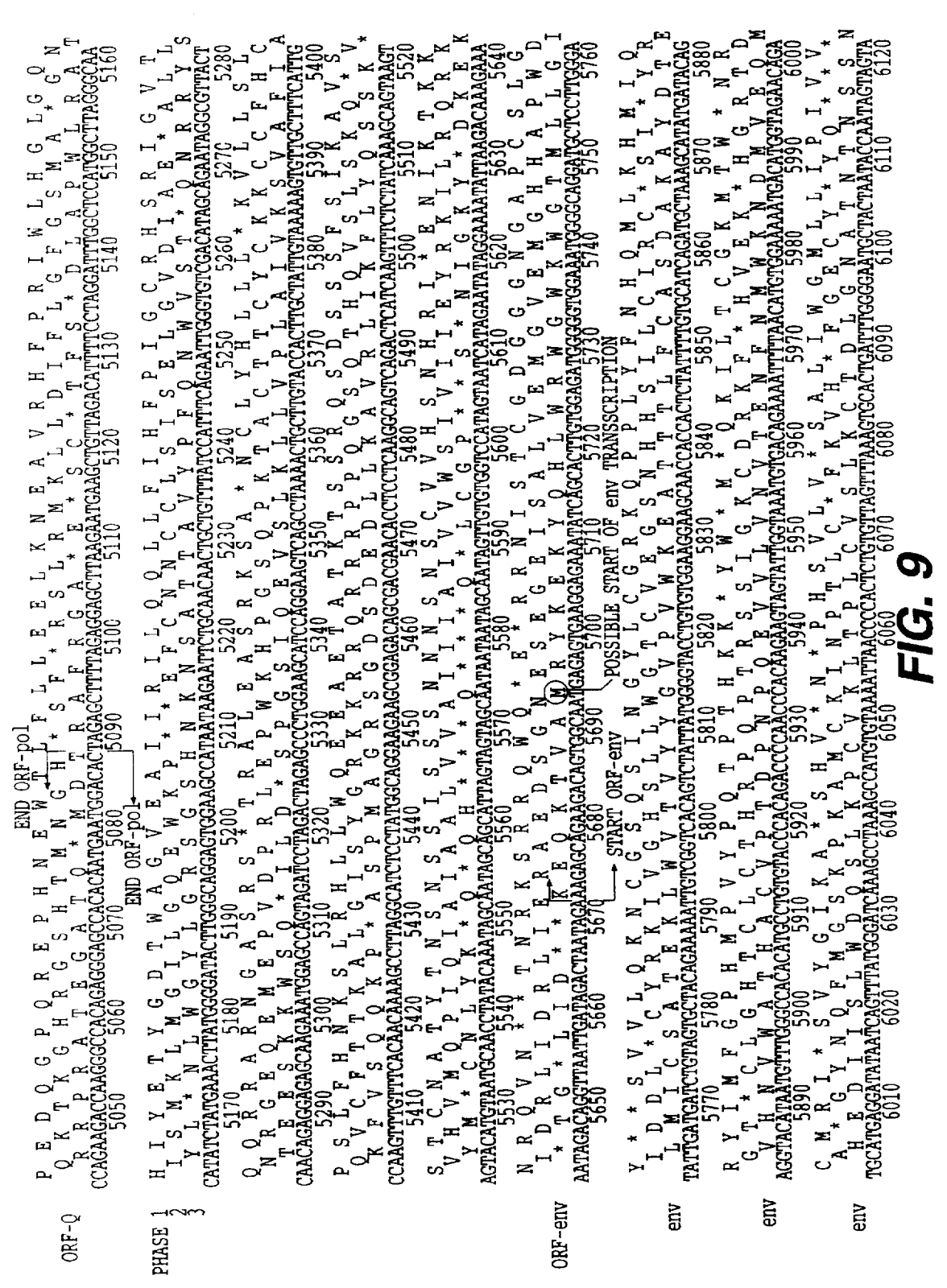
Figure 10:
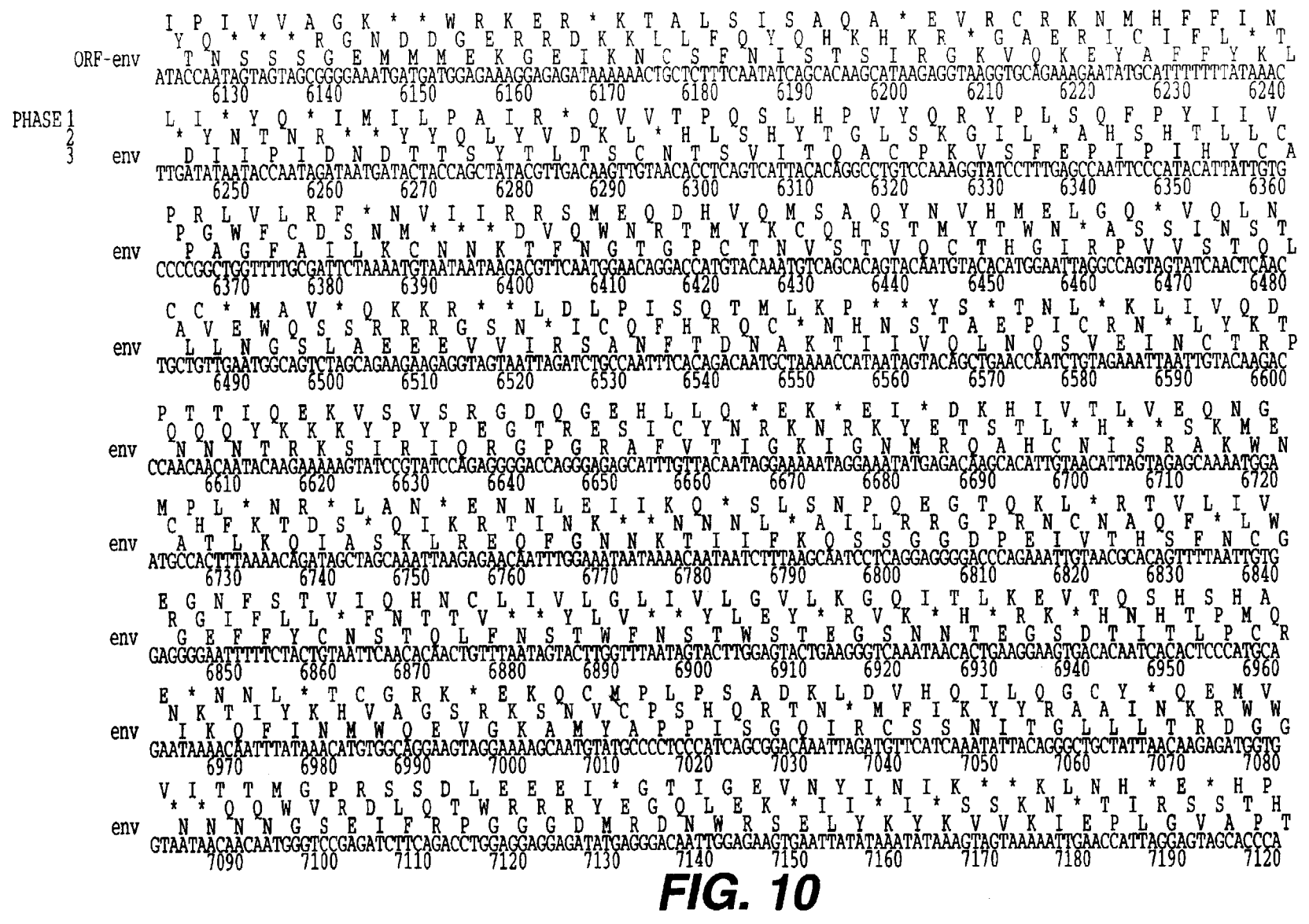
Figure 11:
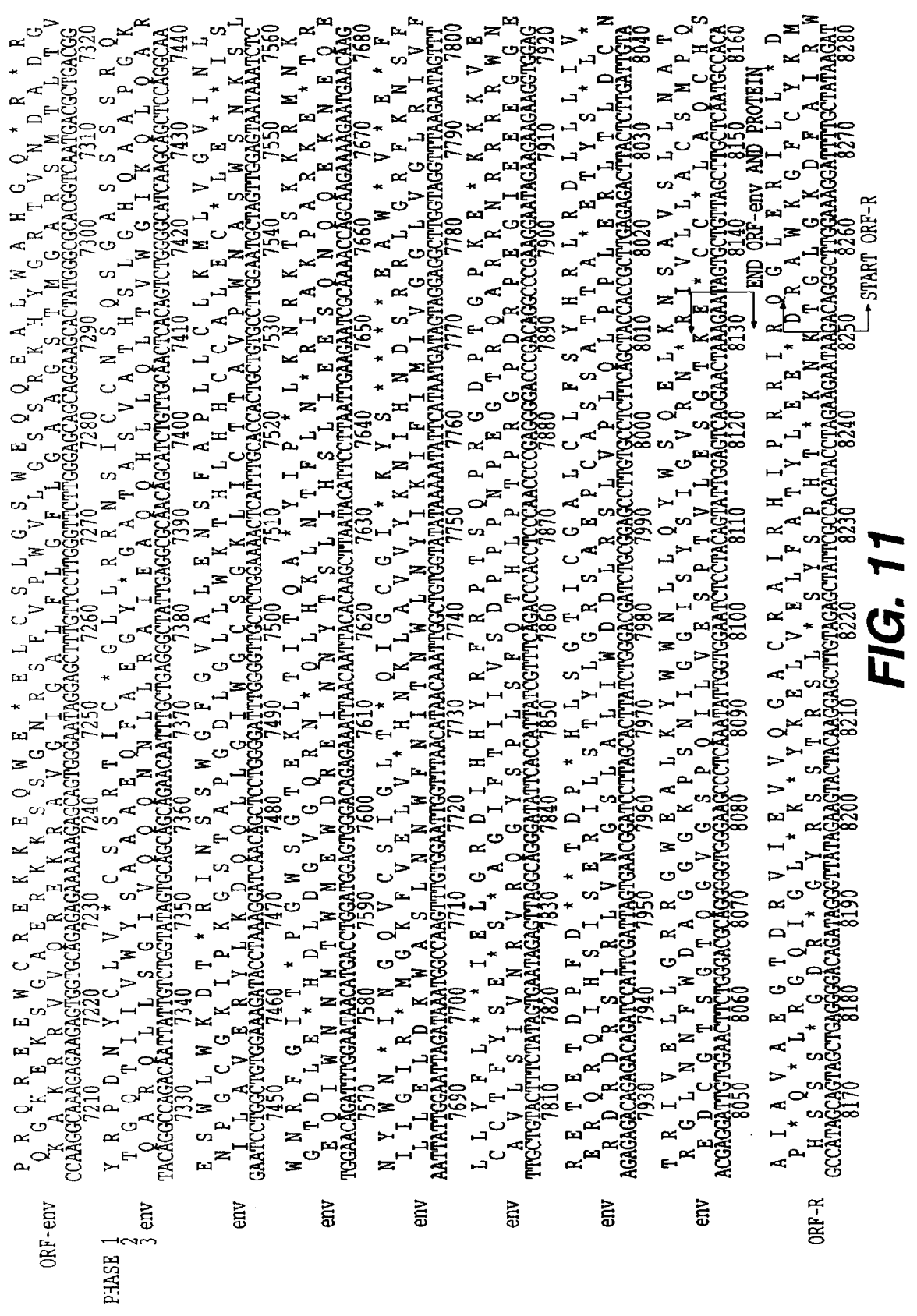
Figure 12:
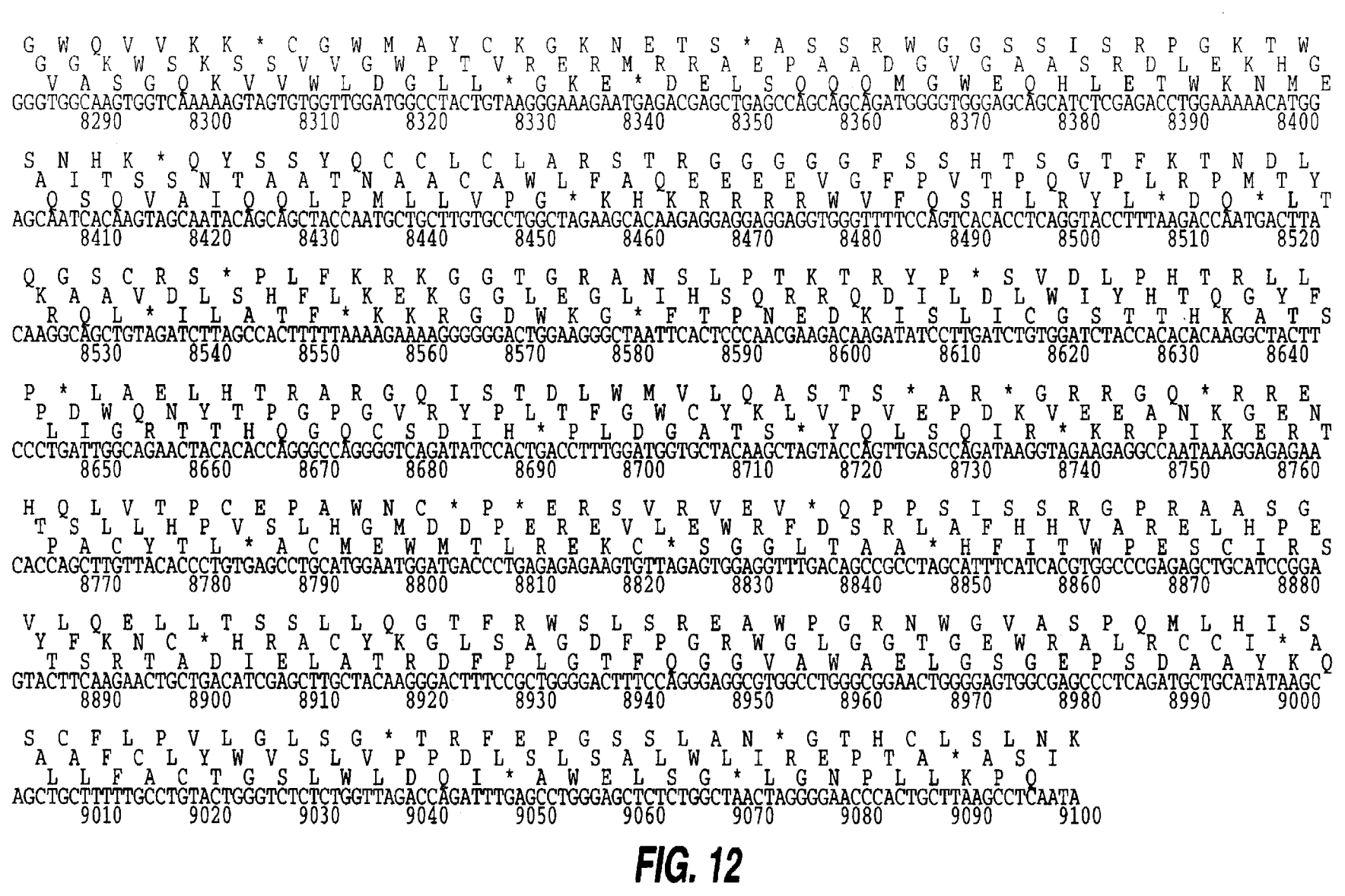

FIGS. 4–12 show the successive nucleotide sequences of a complete LAV genome. The possible peptide sequences in relation to the three possible reading phases related to the nucleotide sequences shown are also indicated;

FIGS. 13–18 reiterate the sequence of part of the LAV genome containing the genes coding for the envelope proteins, with particular boxed peptide sequences which corresponds to groups which normally carry glycosyl groups.

FIGS. 19–26 disclose the complete nucleotide sequence of the LAV genome.

DETAILED DESCRIPTION OF PREFERRED EMBODIMENTS

Figure 1:
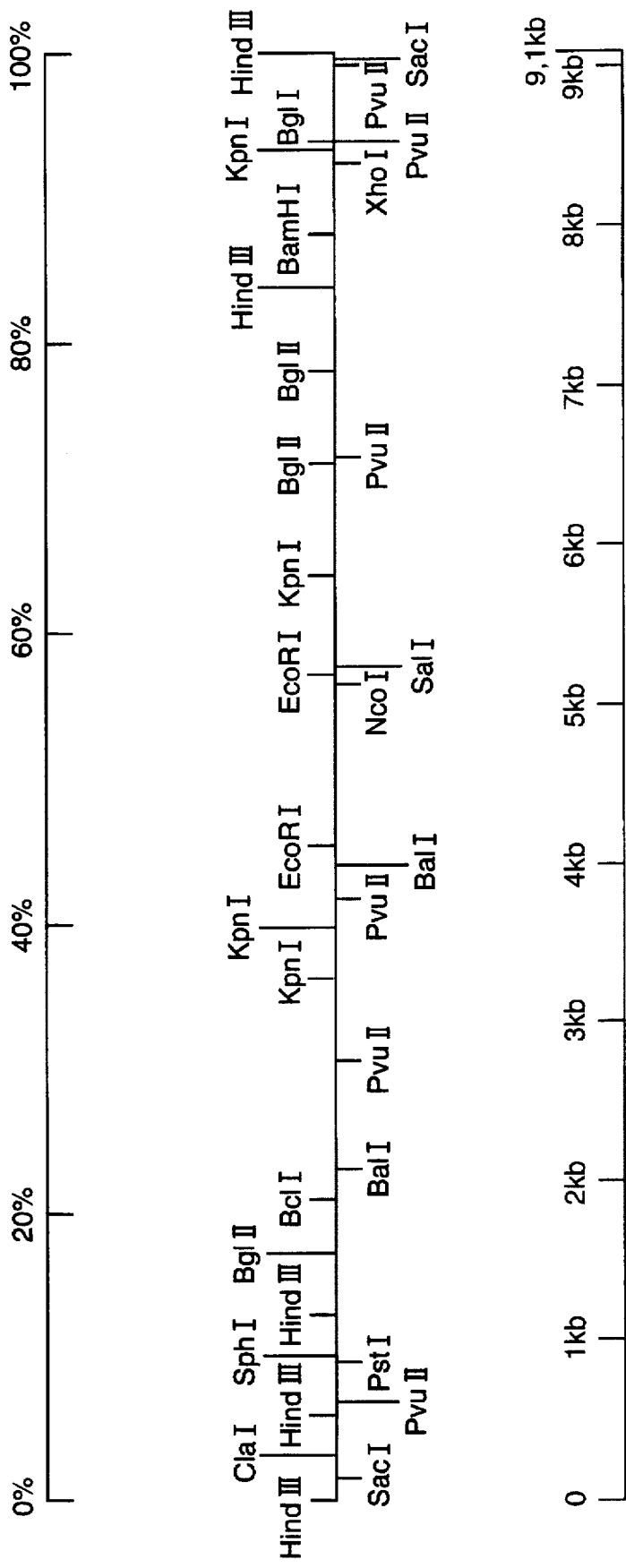
FIG. 1 is the restriction map of a complete LAV genome (clone λJ19)

The sequencing and determination of sites of particular interest were carried out on a phase recombinant corresponding to λJ19 disclosed in the abovesaid British Patent application Nr. 84 23659. A method for preparing it is disclosed in that application.

The whole recombinant phage DNA of clone λJ19 (disclosed in the earlier application) was sonicated according to the protocol of DEININGER (1983). Analytical Biochem. 129, 216. The DNA was repaired by a Klenow reaction for 12 hours at 16° C. The DNA was electrophoresed through 0.8% agarose gel and DNA in the size range of 300–600 bp was cut out and electroeluted and precipitated. Resuspended DNA (in 10 mM Tris, pH 8; 0.1 mM EDTA) was ligated into M13mp8 RF DNA (cut by the restriction enzyme Sma I and subsequently alkaline phosphated), using T4 DNA- and RNA-ligases (Maniatis T et al (1982)— Molecular cloning—Cold Spring Harbor Laboratory). An $E.$ $coli$ strain designated as TG1 was used for further study. This strain has the following genotype: Δlac pro, supE, thi.F'traD36, proAB, lacI$^q$, ZΔM15.r$^-$ This $E.$ $coli$ TGI strain has the peculiarity of enabling recombinants to be recognized easily. The blue colour of the cells transfected with plasmids which did not recombine with a fragment of LAV DNA is not modified. To the contrary cells transfected by a recombinant plasmid containing a LAV DNA fragment yield white colonies. The technique which was used is disclosed in Gene (1983), 26, 101.

This strain was transformed with the ligation mix using the Hanahan method (Hanahan D (1983) J. Mol. Biol. 166, 557). Cells were plated out on tryptone-agarose plate with IPTG and X-gal in soft agarose. While plaques were either picked and screened or screened directly in situ using nitrocellulose filters. Their DNAs were hybridized with nick-translated DNA inserts of pUC18 HindIII subclones of λJ19. This permitted the isolation of the plasmids or subclones of λ which are identified in the table hereafter. In relation to this table it should also be noted that the designation of each plasmid is followed by the deposition number of a cell culture of $E.$ $coli$ TGI containing the corresponding plasmid at the "Collection Nationale des Cultures de Micro-organismes" (C.N.C.M.) of the Pasteur Institute in Paris, France. A non-transformed TGI cell line was also deposited at the C.N.C.M. under Nr. I-364. All these deposits took place on Nov. 15, 1984. The sizes of the corresponding inserts derived from the LAV genome have also been indicated.

TABLE

| | Essential features of the recombinant plasmids | | |
|---|---|---|---|
| pJ19 | 1 plasmid<br>Hind III - Sac I - Hind III | (I-365) | 0.5 kb |
| pJ19 | 17 plasmid<br>Hind III - Pst I - Hind III | (I-367) | 0.6 kb |
| pJ19 | 6 plasmid<br>Hind 111 (5')<br>Bam HI<br>Xho I<br>Kpn I<br>Bgl I<br>Sac I (3')<br>Hind III | (I-366) | 1.5 kb |
| pJ19 | 13 plasmid<br>Hind III (5')<br>Bgl II<br>Kpn I<br>Kpn I<br>Eco RI<br>Eco RI<br>Sal I | (I-368) | 6.7 kb |

TABLE-continued

| Essential features of the recombinant plasmids |
|---|
| Kpn I |
| Bgl II |
| Bgl II |
| Hind III (3') |

Positively hybridizing M13 phage plates were grown up for 5 hours and the single-stranded DNAs were extracted.

M13mp8 subclones of λJ19 DNAs were sequenced according to the dideoxy method and technology devised by Sanger et al. Sanger (1977), Proc. Natl. Acad. Sci. USA, 74, 5463 and M13 cloning and sequencing handbook, AMERSHAM (1983). The 17-mer oligonucleotide primer α-$^{35}$SdATP (400 Ci/mmol, AMERSHAM), and 0.5X–5X buffer gradient gels (Biggen M. D. et al (1983), Proc. Natl. Acad. Sci. USA, 50, 3963) were used. Gels were read and put into the computer under the programs of Staden (Staden R. (1982), Nucl. Acids Res. 10, 4731). All the appropriate references and methods can be found in the AMERSHAM M13 cloning and sequencing handbook.

The complete sequence of λJ19 was deduced from the experiments as further disclosed hereafter.

FIGS. 4–12 provide the DNA nucleotide sequence of the complete genome of LAV. The numbering of the nucleotides starts from a left most HindIII restriction site (5'AAG . . . ) of the restriction map. The numbering occurs in tens whereby the last zero number of each of the numbers occuring on the drawings is located just below the nucleotide corresponding to the nucleotides designated. That is, the nucleotide at position 10 is T, the nucleotide at position 20 is C, etc.

Above each of the lines of the successive nucleotide sequences there are provided three lines of single letters corresponding to the amino acid sequence deduced from the DNA sequence (using the genetic code) for each of the three reading phases, whereby said single letters have the following meanings.

A: alanine
R: arginine
K: lysine
H: histidine
C: cysteine
M: methionine
W: tryptophan
F: phenylalanine
Y: tyrosine
L: leucine
V: valine
I: isoleucine
G: glycine
T: threonine
S: serine
E: glutamic acid
D: Aspartic acid
N: asparagine
Q: glutamine
P: proline.

The asterisk signs "*" correspond to stop codons (i.e. TAA, TAG and TGA).

Figure 4:
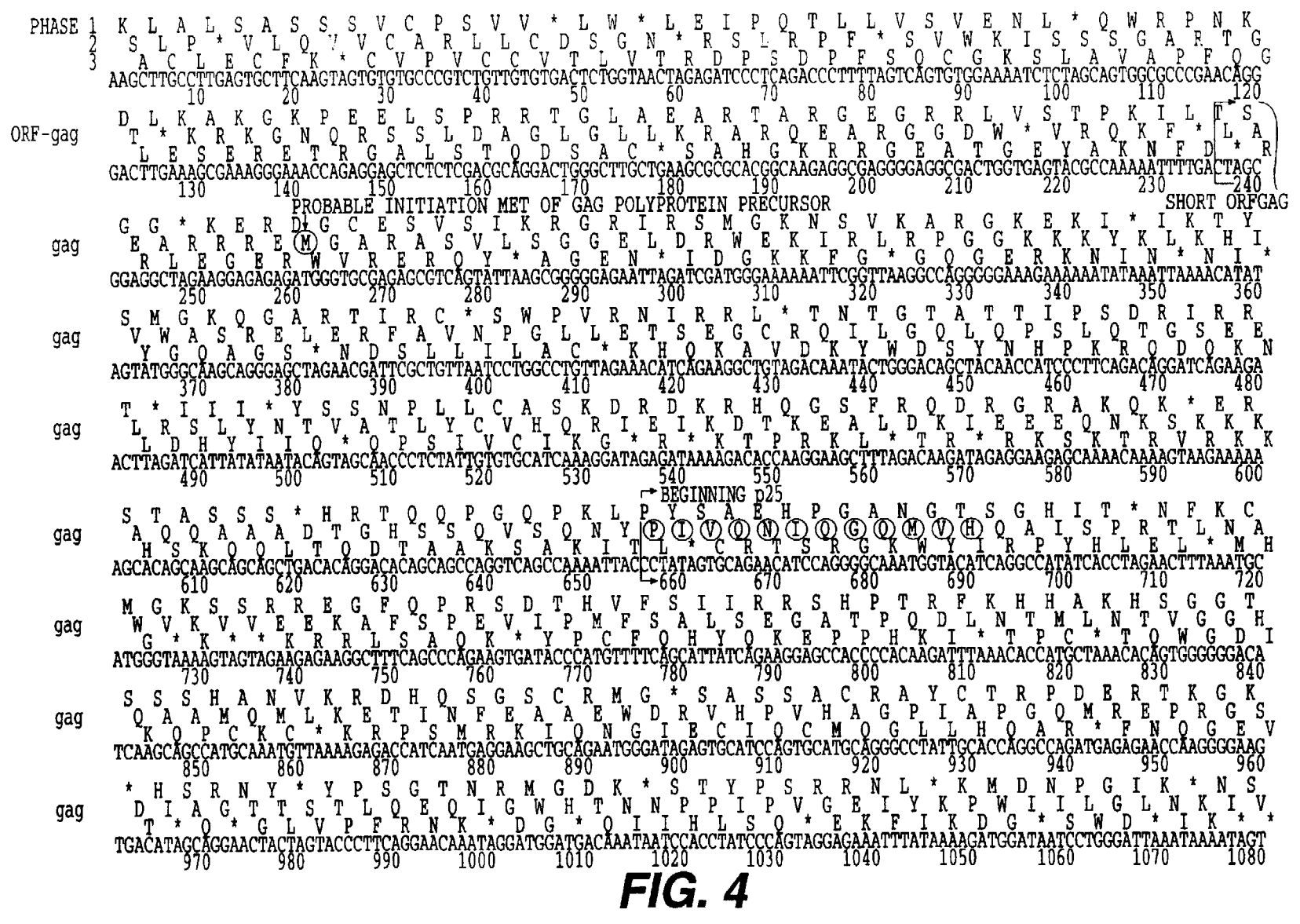

Starting above the first line of the DNA nucleotide sequence of FIG. 4, the three reading phases are respectively marked "1", "2", "3", on the left hand side of the drawing. The same relative presentation of the three theoretical reading phases is then used over all the successive lines of the LAV nucleotide sequence.

Figure 2:
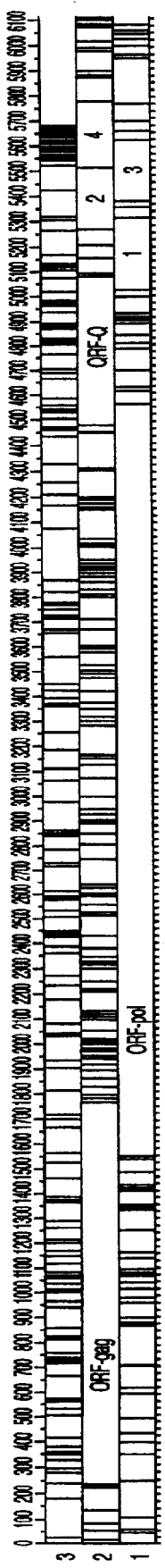
FIGS. 2 and 3 show diagrammatically parts of the three possible reading phases of LAV genomic RNA, including the open reading frames (ORF) apparent in each of said reading phases.
Figure 3:
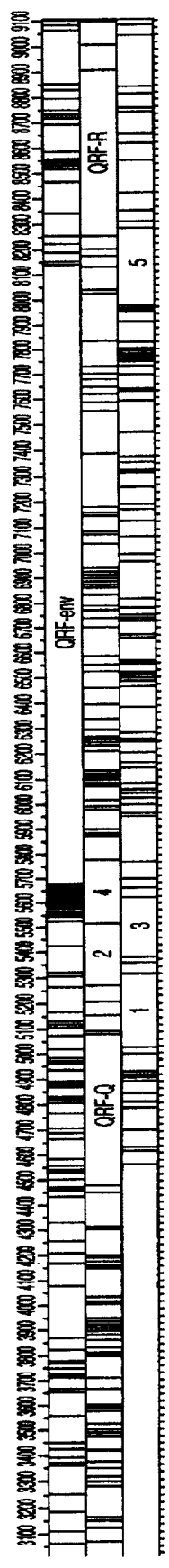

FIGS. 2 and 3 provide a diagrammatized representation of the lengths of the successive open reading frames corresponding to the successive reading phases (also referred to by numbers "1", "2" and "3" appearing in the left hand side part of FIG. 2). The relative positions of these open reading frames (ORF) with respect to the nucleotide structure of the LAV genome is referred to by the scale of numbers representative of the respective positions of the corresponding nucleotides in the DNA sequence. The vertical bars correspond to the positions of the corresponding stop codons.

1) The "gag gene" (or ORF-gag)

The "gag gene" codes for core proteins. Particularly it appears that a genomic fragment (ORF-gag) thought to code for the core antigens including the p25, p18 and p13 proteins is located between nucleotide position 236 (starting with 5' CTA GCG GAG 3') and nucleotide position 1759 (ending by CTCG TCA CAA 3'). The structure of the peptides or proteins encoded by parts of said ORF is deemed to be that corresponding to phase 2.

The methionine amino acid "M" coded by the ATG at position 260-262 is the probable initiation methionine of the gag protein precursor. The end of ORF-gag and accordingly of gag protein appears to be located at position 1759.

The beginning of p25 protein, thought to start by a P-I-V-Q-N-I-Q-G-Q-M-V-H . . . amino acid sequence is thought to be coded for by the nucleotide sequence CCTATA . . . , starting at position 656.

Hydrophilic peptides in the gag open reading frame are identified hereafter. They are defined starting from amino acid 1=Met (M) coded by the ATG starting from 260-2 in the LAV DNA sequence.

Those hydrophilic peptides are

| |
|---|
| 12–32 amino acids inclusive |
| 37–46 amino acids inclusive |
| 49–79 amino acids inclusive |
| 88–153 amino acids inclusive |
| 158–165 amino acids inclusive |
| 178–188 amino acids inclusive |
| 200–220 amino acids inclusive |
| 226–234 amino acids inclusive |
| 239–264 amino acids inclusive |
| 288–331 amino acids inclusive |
| 352–361 amino acids inclusive |
| 377–390 amino acids inclusive |
| 399–432 amino acids inclusive |
| 437–484 amino acids inclusive |
| 492–491 amino acids inclusive |

The invention also relates to any combination of these peptides.

2) The "pol gene" (or ORF-pol)

FIGS. 4–12 also show that the DNA fragments extending from nucleotide position 1555 (starting with 5'TTT TTT . . . 3' to nucleotide position 5086 is thought to correspond to the pol gene. The polypeptidic structure of the corresponding polypeptides is deemed to be that corresponding to phase 1. It stops at position 4563 (end by 5'G GAT GAG GAT 3').

These genes are thought to code for the virus polymerase or reverse transcriptase.

3) The envelope gene (or ORF-env)

The DNA sequence thought to code for envelope proteins is thought to extend from nucleotide position 5670 (starting with 5'AAA GAG GAG A . . . 3') up to nucleotide position 8132 (ending by . . . A ACT AAA GAA 3'). Polypeptide structures of sequences of the envelope protein correspond to those read according to the "phase 3" reading phase.

The start of env transcription is thought to be at the level of the ATG codon at positions 5691–5693.

Additional features of the envelope protein coded by the env genes appear on FIGS. 13–18. These are to be considered as paired FIGS. 13 and 14; 15 and 16; 17 and 18, respectively.

It is to be mentioned that because of format difficulties

FIGS. 14 overlaps to some extent with FIG. 13,

FIG. 16 overlaps to some extent with FIG. 15,

FIG. 18 overlaps to some extent with FIG. 17.

Thus, for instance, FIGS. 13 and 14 must be considered together. Particularly the sequence shown on the first line on the top of FIG. 13 overlaps with the sequence shown on the first line on the top of FIG. 14. In other words, the starting of the reading of the successive sequences of the env gene as represented in FIGS. 13–18 involves first reading the first line at the top of FIG. 13 then proceeding further with the first line of FIG. 14. One then returns to the beginning of the second line of FIG. 13, then again further proceeds with the reading of the second line of page 14, etc. The same observations then apply to the reading of the paired FIGS. 15 and 16, and paired FIGS. 17 and 18, respectively.

The locations of neutralizing epitopes are further apparent in FIGS. 13–18. Reference is more particularly made to the boxed groups of three letters included in the amino acid sequences of the envelope proteins (reading phase 3) which can be designated generally by the formula N-X-S or N-X-T, wherein X is any other possible amino acid. Thus, the initial protein product of the env gene is a glycoprotein of molecular weight in excess of 91,000. These groups are deemed to generally carry glycosylated groups. These N-X-S and N-X-T groups with attached glycosylated groups form together hydrophilic regions of the protein and are deemed to be located at the periphery of and to be exposed outwardly with respect to the normal conformation of the proteins. Consequently, they are considered as being epitopes which can efficiently be brought into play in vaccine compositions.

The invention thus concerns with more particularity peptide sequences included in the env proteins and excizable therefrom (or having the same amino acid structure), having sizes not exceeding 200 amino acids.

Preferred peptides of this invention (referred to hereafter as a, b, c, d, e, f) are deemed to correspond to those encoded by the nucleotide sequences which extend, respectively, between the following positions:

| |
|---|
| a) from about 6095 to about 6200 |
| b) from about 6260 to about 6310 |
| c) from about 6390 to about 6440 |
| d) from about 6485 to about 6620 |
| e) from about 6860 to about 6930 |
| f) from about 1535 to about 7630 |

Other hydrophilic peptides in the env open reading frame are identified hereafter. They are defined starting from amino acid 1=lysine (K) coded by the AAA at position 5670-2 in the LAV DNA sequence.

These hydrophilic peptides are

| |
|---|
| 8–23 amino acids inclusive |
| 63–78 amino acids inclusive |
| 82–90 amino acids inclusive |
| 97–123 amino acids inclusive |
| 127–183 amino acids inclusive |
| 197–201 amino acids inclusive |
| 239–294 amino acids inclusive |
| 300–327 amino acids inclusive |
| 334–381 amino acids inclusive |
| 397–424 amino acids inclusive |
| 466–500 amino acids inclusive |
| 510–523 amino acids inclusive |
| 551–577 amino acids inclusive |
| 594–603 amino acids inclusive |
| 621–630 amino acids inclusive |
| 657–679 amino acids inclusive |
| 719–758 amino acids inclusive |
| 780–803 amino acids inclusive |

The invention also relates to any combinations of these peptides.

4) The other ORF

The invention further concerns DNA sequences which provide open reading frames defined as ORF-Q, ORF-R and as "1", "2", "3", "4", "5", the relative position of which appears more particularly in FIGS. 2 and 3.

These ORFs have the following locations:

| ORF-Q | phase 1 | start 4478 | stop 5086 |
|---|---|---|---|
| ORF-R | phase 2 | start 8249 | stop 8896 |
| ORF-1 | phase 1 | start 5029 | stop 5316 |
| ORF-2 | phase 2 | start 5273 | stop 5515 |
| ORF-3 | phase 1 | start 5383 | stop 5616 |
| ORF-4 | phase 2 | start 5519 | stop 5773 |
| ORF-5 | phase 1 | start 7986 | stop 8279 |

The LTF (long terminal repeats) can be defined as lying between position 8560 and position 160 (end extending over position 9097/1). As a matter of fact the end of the genome is at 9097 and, because of the LTR structure of the retrovirus, links up with the beginning of the sequence:

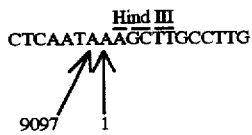

The invention concerns more particularly all the DNA fragments which have been more specifically referred to hereabove and which correspond to open reading frames. It will be understood that the man skilled in the art will be able to obtain them all, for instance by cleaving an entire DNA corresponding to the complete genome of a LAV species, such as by cleavage by a partial or complete digestion thereof with a suitable restriction enzyme and by the subsequent recovery of the relevant fragments. The different DNAs disclosed in the earlier mentioned British Application can be resorted to also as a source of suitable fragments. The techniques disclosed hereabove for the isolation of the fragments which were then included in the plasmids referred to hereabove and which were then used for the DNA sequencing can be used.

Of course other methods can be used. Some of them have been exemplified in the earlier British Application. Reference is, for instance, made to the following methods.

a) DNA can be transfected into mammalian cells with appropriate selection markers by a variety of techniques, such as calcium phosphate precipitation, polyethylene glycol, protoplast-fusion, etc.

b) DNA fragments corresponding to genes can be cloned into expression vectors for *E. coli*, yeast or mammalian cells and the resultant proteins purified.

c) The provival DNA can be "shot-gunned" (fragmented) into procaryotic expression vectors to generate fusion polypeptides. Recombinants producing antigenically competent fusion proteins can be identified by simply screening the recombinants with antibodies against LAV antigens.

The invention also relates more specifically to cloned probes which can be made starting from any DNA fragment according to this invention, thus to recombinant DNAs containing such fragments, particularly any plasmids amplifiable in procaryotic or eucaryotic cells and carrying said fragments.

Using the cloned DNA fragments as a molecular hybridization probe—either by marking with radionucleotides or with fluorescent reagents—LAV virion RNA may be detected directly in the blood, body fluids and blood products (e.g. of the antihemophilic factors, such as Factor VIII concentrates) and vaccines, i.e. hepatitis B vaccine. It has already been shown that whole virus can be detected in culture supernatants of LAV producing cells. A suitable method for achieving that detection comprises immobilizing virus onto a support, e.g. nitrocellulose filters, etc., disrupting the virion, and hybridizing with labelled (radiolabelled or "cold" fluorescent- or enzyme-labelled) probes. Such an approach has already been developed for hepatitis B virus in peripheral blood (according to SCOTTO J. et al. Hepatology (1983), 3, 379–384).

Probes according to the invention can also be used for rapid screening of genomic DNA derived from the tissue of patients with LAV related symptoms to see if the proviral DNA or RNA is present in host tissue and other tissues.

A method which can be used for such screening comprises the following steps: extraction of DNA from tissue, restriction enzyme cleavage of said DNA, electrophoresis of the fragments and Southern blotting of genomic DNA from tissues, and subsequent hybridization with labelled cloned LAV proviral DNA. Hybridization in situ can also be used.

Lymphatic fluids and tissues and other non-lymphatic tissues of humans, primates and other mammalian species can also be screened to see if other evolutionary related retrovirus exist. The methods referred to hereabove can be used, although hybridization and washings would be done under non-stringent conditions.

The DNA according to the invention can also be used for achieving the expression of LAV viral antigens for diagnostic purposes.

The invention also relates to the polypeptides themselves which can be expressed by the different DNAs of the inventions, particularly by the ORFs or fragments thereof, in appropriate hosts, particularly procaryotic or eucaryotic hosts, after transformation thereof with a suitable vector previously modified by the corresponding DNAs.

These polypeptides can be used as diagnostic tools, particularly for the detection of antibodies in biological media, particularly in sera or tissues of persons afflicted with pre-AIDS or AIDS, or simply carrying antibodies in the absence of any apparent disorders. Conversely, the different peptides according to this invention can be used themselves for the production of antibodies, preferably monoclonal antibodies specific of the different peptides respectively. For the production of hybridomas secreting said monoclonal antibodies, conventional production and screening methods are used. These monoclonal antibodies, which themselves are part of the invention, then provide very useful tools for the identification and even determination of relative proportions of the different polypeptides or proteins in biological samples, particularly human samples containing LAV or related viruses.

Thus, all of the above peptides can be used in diagnostics as sources of immunogens or antigens free of viral particles, produced using non-permissive systems, and thus of litter or no biohazard risk.

The invention further relates to the hosts (procaryotic or eucaryotic cells) which are transformed by the above-mentioned recombinants and which are capable of expressing said DNA fragments.

Finally, it also relates to vaccine compositions whose active principle is to be constituted by any of the expressed antigens, i.e. whole antigens, fusion polypeptides or oligopeptides, in association with a suitable pharmaceutical or physiologically acceptable carrier.

Preferably, the active principles to be considered in that field consist of the peptides containing less than 250 amino acid units, preferably less than 150 as deducible from the complete genomes of LAV, and even more preferably those peptides which contain one or more groups selected from N-X-S and N-X-T as defined above. Preferred peptides for use in the production of vaccinating principles are peptides (a) to (f) as defined above. By way of example having no limitative character, there may be mentioned that suitable dosages of the vaccine compositions are those which enable administration to the host, particularly human host ranging from 10 to 500 micrograms per kg, for instance 50 to 100 micrograms per kg.

For the purpose of clarity, FIGS. 19 to 26 are added. Reference may made thereto in case of difficulties or reading blurred parts of FIGS. 4 to 12.

Needless to say that FIGS. 19–26 are merely a reiteration of the whole DNA sequence of the LAV genome.

Finally, the invention also concerns vectors for the transformation of eucaryotic cells of human origin, particularly lymphocytes, the polymerases of which are capable of recognizing the LTRs of LAV. Particularly, said vectors are characterized by the presence of a LAV LTR therein, said LTR being then active as a promoter enabling the efficient transcription and translation in a suitable host of the above defined DNA insert coding for a determined protein placed under its controls.

Needless to say that the invention extends to all variants of genomes and corresponding DNA fragments (ORFs) having substantially equivalent properties, all of said genomes belonging to retroviruses which can be considered as equivalents of LAV.

We claim:

1. A peptide of HIV-1 expressed from DNA corresponding to the nef open reading frame, the DNA having the following nucleotide sequence:

```
8250
GA 8260        8270        8280
CAGGGCTTGG AAAGGATTTT GCTATAAGAT 8290        8300
            GGGTGGCAAG TGGTCAAAAA 8310        8320        8330
GTAGTGTGGT TGGATGGCCT ACTGTAAGGG 8340        8350
            AAAGAATGAG ACGAGCTGAG 8360        8370        8380
CCAGCAGCAG ATGGGGTGGG AGCAGCATCT 8390        8400
            CGAGACCTGG AAAAACATGG 8410        8420        8450
AGCAATCACA AGTAGCAATA CAGCAGCTAC 8430        8450
            CAATGCTGCT TGTGCCTGGC 8460        8470        8480
TAGAAGCACA AGAGGAGGAG GAGGTGGGTT 8490        8500
            TTCCAGTCAC ACCTCAGGTA 8510        8520        8530
CCTTTAAGAC CAATGACTTA CAAGGCAGCT 8540        8550
            GTAGATCTTA GCCACTTTTT 8560        8570        8580
AAAAGAAAAG GGGGGACTGG AAGGGCTAAT 8580        8600
                        TCACTCCCAA CGAAGACAAG 8610        8620        8630
ATATCCTTGA TCTGTGGATC TACCACACAC 8640        8650
                        AAGGCTACTT CCCTGATTGG 8660        8670        8680
CAGAACTACA CACCAGGGCC AGGGGTCAGA 8690        8700
                        TATCCACTGA CCTTTGGATG 8710        8720        8730
GTGCTACAAG CTAGTACCAG TTGAGCCAGA 8740        8750
                        TAAGGTAGAA GAGGCCAATA 8760        8770        8780
AAGGAGAGAA CACCAGCTTG TTACACCCTG 8790        8800
                        TGAGCCTGCA TGGAATGGAT 8810        8820        8830
GACCCTGAGA GAGAAGTGTT AGAGTGGAGG 8840        8850
                        TTTGACAGCC GCCTAGCATT 8860        8870        8880
TCATCACGTG GCCCGAGAGC TGCATCCGGA

8890
                        GTACTTCAAG AACTGC.
```

2. A peptide encoded by the nef gene of HIV-1, wherein the peptide is free of particles of said virus and has the following amino acid sequence:

Asp—Arg—Ala—Trp—Lys—Gly—Phe—Cys—Tyr—Lys—Met—

Gly—Gly—Lys—Trp—Ser—Lys—Ser—Ser—Val—Val—Gly—

Trp—Pro—Thr—Val—Arg—Glu—Arg—Met—Arg—Arg—Ala—

-continued

Glu—Pro—Ala—Ala—Asp—Gly—Val—Gly—Ala—Ala—Ser—
Arg—Asp—Leu—Glu—Lys—His—Gly—Ala—Ile—Thr—Ser—
Ser—Asn—Thr—Ala—Ala—Thr—Asn—Ala—Ala—Cys—Ala—
Trp—Leu—Glu—Ala—Gln—Glu—Glu—Glu—Val—Gly—
Phe—Pro—Val—Thr—Pro—Gln—Val—Pro—Leu—Arg—Pro—
Met—Thr—Tyr—Lys—Ala—Ala—Val—Asp—Leu—Ser—His—
Phe—Leu—Lys—Glu—Lys—Gly—Gly—Leu—Glu—Gly—Leu—
Ile—His—Ser—Gln—Arg—Arg—Gln—Asp—Ile—Leu—Asp—
Leu—Trp—Ile—Tyr—His—Thr—Gln—Gly—Tyr—Phe—Pro—

-continued

Asp—Trp—Gln—Asn—Tyr—Thr—Pro—Gly—Pro—Gly—Val—
Arg—Tyr—Pro—Leu—Thr—Phe—Gly—Trp—Cys—Tyr—Lys—
Leu—Val—Pro—Val—Glu—Pro—Asp—Lys—Val—Glu—Glu—
Ala—Asn—Lys—Gly—Glu—Asn—Thr—Ser—Leu—Leu—His—
Pro—Val—Ser—Leu—His—Gly—Met—Asp—Asp—Pro—Glu—
Arg—Glu—Val—Leu—Glu—Trp—Arg—Phe—Asp—Ser—Arg—
Leu—Ala—Phe—His—His—Val—Ala—Arg—Glu—Leu—His—
Pro—Glu—Tyr—Phe—Lys—Asn—Cys.

\* \* \* \* \*

UNITED STATES PATENT AND TRADEMARK OFFICE
CERTIFICATE OF CORRECTION

PATENT NO.: 5,705,612

DATED: January 6, 1998

INVENTOR(S): Marc ALIZON et al.

It is certified that an error appears in the above-identified patent and that said Letters Patent is hereby corrected as shown below:

Claim 1, col. 10, line 12, "8450" should be --8430--.

Claim 1, col. 10, line 14, "8430" should be --8440--.

Claim 1, col. 10, line 28, "8580" should be --8590--.

Signed and Sealed this

Nineteenth Day of May, 1998

Attest:

BRUCE LEHMAN

Attesting Officer

Commissioner of Patents and Trademarks